United States Patent
Hancock et al.

(10) Patent No.: US 10,937,133 B2
(45) Date of Patent: Mar. 2, 2021

(54) ADAPTIVE RINGDOWN SUBTRACTION FOR CORONARY AND PERIPHERAL INTRAVASCULAR ULTRASOUND (IVUS)

(71) Applicant: KONINKLIJKE PHILIPS N.V., Eindhoven (NL)

(72) Inventors: Andrew Hancock, Sacramento, CA (US); Jinhyoung Park, Rancho Cordova, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 119 days.

(21) Appl. No.: 16/349,789

(22) PCT Filed: Nov. 15, 2017

(86) PCT No.: PCT/EP2017/079247
§ 371 (c)(1),
(2) Date: May 14, 2019

(87) PCT Pub. No.: WO2018/091487
PCT Pub. Date: May 24, 2018

(65) Prior Publication Data
US 2019/0362474 A1 Nov. 28, 2019

Related U.S. Application Data

(60) Provisional application No. 62/423,145, filed on Nov. 16, 2016.

(51) Int. Cl.
*G06K 9/00* (2006.01)
*G06T 5/00* (2006.01)
(Continued)

(52) U.S. Cl.
CPC ............ *G06T 5/005* (2013.01); *A61B 8/5207* (2013.01); *G06T 5/50* (2013.01); *G16H 30/40* (2018.01);
(Continued)

(58) Field of Classification Search
None
See application file for complete search history.

(56) References Cited

U.S. PATENT DOCUMENTS 5,183,048 A * 2/1993 Eberle ...................... 128/662.06
10,420,530 B2 * 9/2019 Hancock .................. A61B 8/12
(Continued)

OTHER PUBLICATIONS

International Search Report and Written Opinion, International Application No. PCT/EP2017/079247, dated Jan. 16, 2018.
(Continued)

*Primary Examiner* — Shervin K Nakhjavan

(57) ABSTRACT

Ultrasound imaging devices, systems, and methods are provided. In one embodiment, a method of reducing ringdown artifacts in an ultrasound imaging system includes obtaining a plurality of frames of samples including tissue information and a ringdown component; determining a reference frame based on the plurality of frames to approximate the ringdown component; subtracting the reference frame from a current frame of the plurality of frames to produce a difference frame; selecting between the current frame and the difference frame to obtain a ringdown-reduced frame to represent the tissue information; and forming an ultrasound image from the ringdown-reduced frame. In one embodiment, an ultrasound image processing system including a processing unit configured to compute a difference frame based on a current frame and a reference frame; and select between the current frame and the difference frame to obtain a ringdown-reduced frame to represent the tissue information.

18 Claims, 17 Drawing Sheets

(51) Int. Cl.
*G16H 30/40* (2018.01)
*A61B 8/08* (2006.01)
*G06T 5/50* (2006.01)

(52) U.S. Cl.
CPC ............... *G06T 2207/10016* (2013.01); *G06T 2207/10132* (2013.01); *G06T 2207/20004* (2013.01); *G06T 2207/20224* (2013.01); *G06T 2207/30048* (2013.01); *G06T 2207/30101* (2013.01)

(56) References Cited

U.S. PATENT DOCUMENTS

2005/0240105 A1\* 10/2005 Mast .............................. 600/443
2008/0075375 A1\* 3/2008 Unal ...................... G06K 9/621
382/243

OTHER PUBLICATIONS

"SPEC, ACE Ringdown Theory of Operation", Volcano, Control # 202-0018.07/002, 2016.
Hancock, A., "TruVu Design for IP 2016 Re-submittal", Image Guided Therapy, Philips Volcano Corporation, Jul. 2016.

\* cited by examiner

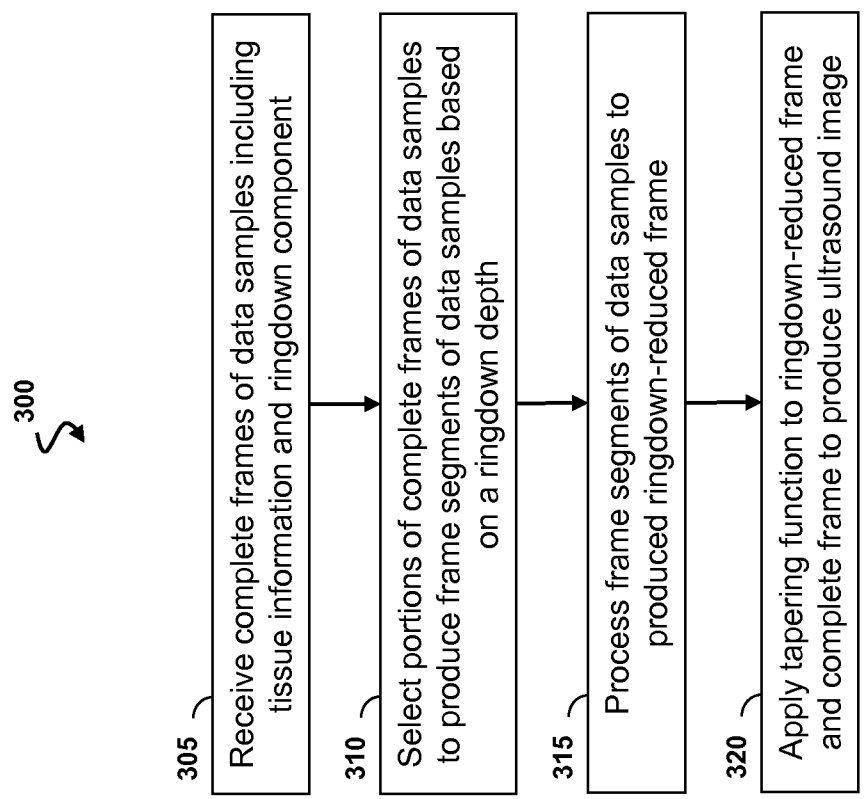

ADAPTIVE RINGDOWN SUBTRACTION FOR CORONARY AND PERIPHERAL INTRAVASCULAR ULTRASOUND (IVUS)

CROSS-REFERENCE TO PRIOR APPLICATIONS

This application is the U.S. National Phase application under 35 U.S.C. § 371 of International Application No. PCT/EP2017/079247, filed on 15 Nov. 2017, which claims the benefit of U.S. Provisional Patent Application No. 62/423,145, filed on 16 Nov. 2016. These applications are hereby incorporated by reference herein.

TECHNICAL FIELD

The present disclosure relates generally to intravascular ultrasound (IVUS) imaging and, in particular, to reducing ringdown artifacts at a range close to an excitation source. In various embodiments, a ringdown reduction processing system receives data from an array of ultrasound transducers, such as piezoelectric zirconate transducers (PZTs), capacitive micromachined ultrasonic transducers (CMUTs), and/or piezoelectric micromachined ultrasound transducers (PMUTs). The ringdown reduction processing system processes the data to select information associated with tissues and discard components corresponding to ringdown artifacts. The ringdown processing system is suitable for use in imaging human blood vessels including coronary vessels and peripheral vessels.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device includes one or more ultrasound transducers arranged at a distal end of an elongate member. The elongate member is passed into the vessel thereby guiding the transducers to the area to be imaged. Once in place, the transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducers and passed along to an IVUS imaging system. The imaging system processes the received ultrasound echoes to produce a cross-sectional image of the vessel where the device is placed.

There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. In side-looking rotational devices, the transducer element is oriented such that the ultrasound beam propagates generally perpendicular to the longitudinal axis of the device. In forward-looking rotational devices, the transducer element is pitched towards the distal tip so that the ultrasound beam propagates more towards the tip, in some devices, being emitted parallel to the longitudinal centerline. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the tissue, vessel, heart structure, etc. from a sequence of pulse/acquisition cycles occurring during a single revolution of the transducer.

In contrast, solid-state IVUS devices utilize a scanner assembly that includes an array of ultrasound transducers connected to a set of transducer controllers. In side-looking and some forward-looking IVUS devices, the transducers are distributed around the circumference of the device. In other forward-looking IVUS devices, the transducers are a linear array arranged at the distal tip and pitched so that the ultrasound beam propagates closer to parallel with the longitudinal centerline. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the imaging system with a simple electrical cable and a standard detachable electrical connector.

Owing to a variety of acoustic and device characteristics, both rotational and solid-state technologies are prone to artifacts and distortions that affect the resulting image. For example, ringdown artifacts are commonly observed in an image at a region near the surface of a transducer. Ringdown artifacts can hide or obscure views of tissues, and thus may cause mis-measurement or mis-interpretation. Ringdown artifacts occur because the same transducer both transmits and receives ultrasonic waves. To generate an ultrasonic wave, an electrical pulse is applied to an ultrasonic crystal transducer such as a PZT. The electrical pulse causes the transducer to oscillate. After generating the desired ultrasonic wave, the transducer continues to oscillate for a period of time until the oscillation dampens out. The oscillation generates a transient signal, which is referred to as a ringdown signal. The transmitted ultrasonic wave is partially reflected by the tissues, generating echoes. The echoes can return to the transducer before the oscillation dampens out. The oscillation can corrupt the echoes received by the transducer, resulting in ringdown artifacts. In a phased array device, transducers are mechanically coupled to each other. When one of the transducers in the array is excited by an electrical pulse, the oscillation of the excited transducer can cause the mechanically coupled transducers in the array to oscillate. Thus, ringdown artifacts in a phased array device can be caused by all transducers in the device.

While existing ultrasound imaging systems have proved useful, there remains a need for improved systems and techniques for identifying and separating tissue structures from ringdown artifacts to provide high quality images.

SUMMARY

Embodiments of the present disclosure provide a ringdown reduction system with tissue identification and ringdown reduction, which may be used in applications such as a solid-state intravascular ultrasound imaging system and rotational intravascular ultrasound imaging system. The ringdown reduction system identifies and separates tissue information from ringdown artifacts in imaging data through data masking and data selection. Accordingly, the ringdown reduction system can provide high-quality images.

In one embodiment, a method of reducing ringdown artifacts in an ultrasound imaging system is provided. The method includes obtaining a plurality of frames of samples including tissue information and a ringdown component; determining a reference frame based on the plurality of frames to approximate the ringdown component; subtracting the reference frame from a current frame of the plurality of frames to produce a difference frame; selecting between the current frame and the difference frame to obtain a ringdown-reduced frame to represent the tissue information; and forming an ultrasound image from the ringdown-reduced frame.

In some embodiments, the method further includes computing a threshold mask from the difference frame; applying the threshold mask to the reference frame to produce a masked reference frame; and applying the threshold mask to the current frame to produce a masked current frame, wherein the selecting includes performing a minimum selection between the masked current frame and the difference frame, and/or clipping magnitudes of the difference frame. In some embodiments, the computing the threshold mask includes determining whether a first absolute magnitude of the difference frame is less than a threshold; setting a mask value of the threshold mask to zero when the first absolute magnitude is less than the threshold; and setting the mask value to one when the first absolute magnitude is greater than or equal to the threshold. In some embodiments, the performing the minimum selection includes determining whether a second absolute magnitude of a first sample of the masked current frame is less than a third absolute magnitude of a second sample of the difference frame; selecting the first sample to produce a third sample in the ringdown-reduced frame when the second absolute magnitude is less than the third absolute magnitude; and selecting the second sample to produce the third sample in the ringdown-reduced frame when the third absolute magnitude is greater than or equal to the second absolute magnitude. In some embodiments, the method further include determining whether a second absolute magnitude of the masked current frame is greater than or equal to a third absolute magnitude of the masked reference frame; and setting a first sample of the ringdown-reduced frame to a value of zero when the second absolute magnitude is less than the third absolute magnitude, and/or reducing the fourth absolute magnitude by a third factor prior to determining whether the second absolute magnitude of the masked current frame is greater than or equal to the fourth absolute magnitude of the masked reference frame, and/or applying an A-line filter to the ringdown-reduced frame prior to forming the ultrasound image. In some embodiments, the obtaining the plurality of frames includes receiving a complete frame of samples; and selecting a portion of the complete frame to obtain the current frame according to a ringdown depth. In some embodiments, the forming the ultrasound image includes multiplying the ringdown-reduced frame by a first tapering factor to produce a tapered ringdown-reduced frame; multiplying the complete frame by a second tapering factor to produce a tapered complete frame; forming a first portion of the ultrasound image corresponding to the ringdown depth by summing the tapered ringdown-reduced frame and a second portion of the tapered complete frame corresponding to the ringdown depth; and forming a remaining portion of the ultrasound image from the tapered complete frame. In some embodiments, the method further includes assigning a lower significant bit of a first sample of the reference frame to a bit value of zero prior to subtracting the reference frame from the current frame. In some embodiments, the determining the reference frame includes multiplying the current frame by a first coefficient to produce a weighted current frame; multiplying a previous averaged frame by a second coefficient to produce a weighted previous averaged frame; updating the previous averaged frame to a current averaged frame by summing the weighted current frame and the weighted previous averaged frame; and assigning the current averaged frame to the reference frame. In some embodiments, the summing the weighted current frame and the weighted previous averaged frame produces a first frame, and wherein the updating the previous averaged frame to the current averaged frame includes subtracting the previous averaged frame from the first frame to produce a second frame; multiplying the second frame by a rate limit factor to produce a third frame; summing the third frame and the previous averaged frame to produce a fourth frame; determining whether a first sample in the second frame is greater than a snap threshold; updating a second sample of the current averaged frame with a third sample of the fourth frame when the first sample is greater the snap threshold; and updating the second sample with a fourth sample of the first frame when the first sample is less than or equal to the snap threshold. In some embodiments, the updating the previous averaged frame to the current averaged frame further includes scaling the third sample with a range taper factor prior to updating second sample of the current averaged frame with the third frame when the first sample is greater than the snap threshold; and scaling the fourth frame with the range taper factor prior to updating the current averaged frame with the fourth sample when the first sample is less than or equal to the snap threshold.

In one embodiment, an ultrasound image processing system includes an interface operable to receive a plurality of frames of samples including tissue information and a ringdown component; and a processing unit coupled to the interface and configured to determine a reference frame based on the plurality of frames to approximate the ringdown component; compute a difference frame based on a current frame of the plurality of frames and the reference frame; and select between the current frame and the difference frame to obtain a ringdown-reduced frame to represent the tissue information. In some embodiments, the processing unit is further configured to compute a threshold mask from the difference frame according to a threshold; apply the threshold mask to the reference frame to produce a masked reference frame; apply the threshold mask to the current frame to produce a masked current frame; and select between the current frame and the difference frame by performing a minimum selection between the masked current frame and the difference frame, and/or clip magnitudes of the difference frame, and/or determine whether a first absolute magnitude of the difference frame is less than the threshold; set a mask value of the threshold mask to a first value when the first absolute magnitude is less than the threshold; and set the mask value to a second value when the first absolute magnitude is greater than or equal to the threshold, and/or determine whether a second absolute magnitude of a first sample of the masked current frame is less than a third absolute magnitude of a second sample of the difference frame; select the first sample to produce a third sample in the ringdown-reduced frame when the second absolute magnitude is less than the third absolute magnitude; and select the second sample to produce the third sample in the ringdown-reduced frame when the third absolute magnitude is greater than or equal to the second absolute magnitude, and/or determine whether a second absolute magnitude of the masked current frame is greater than or equal to a third absolute magnitude of the masked reference frame; and set a first sample of the ringdown-reduced frame to a value of zero when the second absolute magnitude is less than the third absolute magnitude. In some embodiments, the interface is further configured receive a complete frame, wherein the current frame is a portion within a ringdown depth of the complete frame, and wherein the processing unit is further configured to multiply the ringdown-reduced frame by a first tapering factor to produce a tapered ringdown-reduced frame; multiply the complete frame by a second tapering factor to produce a tapered complete frame; forming a first portion of an image corresponding to the ringdown depth by summing the tapered ringdown-reduced frame and a second portion of the tapered complete frame corresponding to the ringdown depth; and forming a remaining portion of an image from the tapered complete frame, and/or apply an A-line filter to the ringdown-reduced frame prior to multiplying the ringdown-reduced frame with the first tapering factor.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 3 is a flow diagram of a method of processing ultrasound imaging data according to embodiments of the present disclosure.

DETAILED DESCRIPTION

Figure 1:
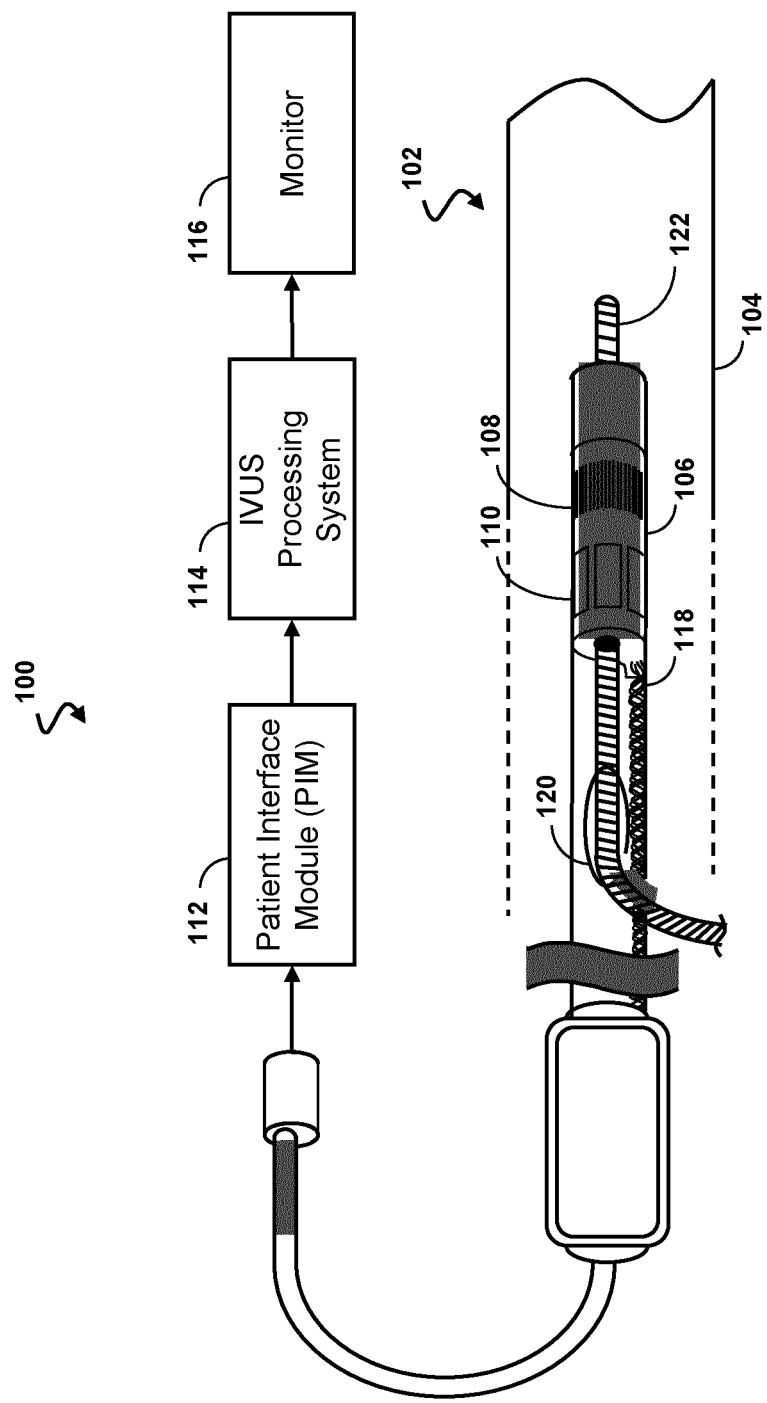
FIG. 1 is a schematic diagram of an intravascular ultrasound (IVUS) imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the IVUS system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an IVUS imaging system 100 according to embodiments of the present disclosure. The system 100 may include an IVUS device elongate member 102 such as a catheter, guide wire, or guide catheter, a patient interface module (PIM) 112, an IVUS processing system 114, such as a console and/or a computer, and a monitor 116.

At a high level, an elongate member 102 is advanced into a vessel 104. The distal-most end of the elongate member 102 includes a scanner assembly 106 with an array of ultrasound transducers 108 and associated control circuitry 110. When the scanner assembly 106 is positioned near the area to be imaged, the ultrasound transducers are activated and ultrasonic energy is produced. A portion of the ultrasonic energy is reflected by the vessel 104 and the surrounding anatomy, and the ultrasound echo signals are received by the transducers 108. Although the scanner assembly 106 is illustrated with the array of transducers 108, the scanner assembly 106 may be alternatively configured to include a rotational transducer to achieve similar functionalities. The PIM 112 transfers the received echo signals to the IVUS processing system 114 where the ultrasound image (including the flow information) is reconstructed and displayed on the monitor 116. The IVUS processing system 114 can include a processor and a memory. The IVUS system 114 can be operable to facilitate the features of the system 100 described herein. For example, the processor can execute computer readable instructions stored on the non-transitory tangible computer readable medium.

In various surgical settings, patient safety requirements mandate physical and electrical isolation of the patient. Thus, if complete electrical isolation is required, the system 100 may be divided into the PIM 112 and the IVUS processing system 114 with an optical, RF, or other non-conductive link for communication between the two. In less stringent environments, conductive communication links and/or power couplings may extend between the two. Moreover, in some embodiments, the PIM 112 and IVUS processing system 114 are collocated and/or part of the same system, unit, chassis, or module. The allocation of image processing tasks between the PIM 112 and the IVUS processing system 114 is merely arbitrary.

The system 100 may use any of a variety of ultrasonic imaging technologies. Accordingly, in some embodiments of the present disclosure, the system 100 is a solid-state IVUS imaging system incorporating an array of piezoelectric transducers fabricated from lead-zirconate-titanate (PZT) ceramic. In some embodiments, the system 100 incorporates capacitive micromachined ultrasonic transducers (CMUTs), or piezoelectric micromachined ultrasound transducers (PMUTs).

In some embodiments, the system 100 includes some features similar to traditional solid-state IVUS system, such as the EagleEye® catheter available from Volcano Corporation and those disclosed in U.S. Pat. No. 7,846,101 hereby incorporated by reference in its entirety. For example, the elongate member 102 includes the ultrasound scanner assembly 106 at a distal end of the member 102, which is coupled to the PIM 112 and the IVUS processing system 114 by a cable 118 extending along the longitudinal body of the member 102. The cable 118 caries control signals, echo data, and power between the scanner assembly 106 and the remainder of the system 100.

In an embodiment, the elongate member 102 further includes a guide wire exit port 120. The guide wire exit port 120 allows a guide wire 122 to be inserted towards the distal end in order to direct the member 102 through a vascular structure (i.e., a vessel) 104. Accordingly, in some instances the IVUS device is a rapid-exchange catheter. In an embodiment, the elongate member 102 can also include an expandable member such as an inflatable balloon near the distal tip to facilitate medical and/or diagnostic procedures.

The PIM 112 facilitates communication of signals between the IVUS processing system 114 and the elongate member 102 to control the operation of the scanner assembly 106. This includes generating control signals to configure the scanner, generating signals to trigger the transmitter circuits, and/or forwarding echo signals captured by the scanner assembly 106 to the IVUS processing system 114. With regard to the echo signals, the PIM 112 forwards the received signals and, in some embodiments, performs preliminary signal processing prior to transmitting the signals to the IVUS processing system 114. In examples of such embodiments, the PIM 112 performs amplification, filtering, and/or aggregating of the data. In an embodiment, the PIM 112 also supplies high- and low-voltage direct current (DC) power to support operation of the circuitry within the scanner assembly 106. The PIM 112 may also perform some, all, or none, of the functions attributed to the IVUS processing system 114 such as processing the echo data to create an ultrasound image.

The IVUS processing system 114 receives the echo data from the scanner assembly 106 by way of the PIM 112 and performs any remaining processing of the data to create an image of the tissue surrounding the scanner assembly 106. The IVUS processing system 114 may also display the image on the monitor 116.

The system 100 may be utilized in a variety of applications and can be used to image vessels and structures within a living body. Vessel 104 represents fluid filled or surrounded structures, both natural and man-made, within a living body that may be imaged and can include for example, but without limitation, structures such as: organs including the liver, heart, kidneys, cardiovascular vessels, as well as valves within the blood or other systems of the body. In addition to imaging natural structures, the images may also include imaging man-made structures such as, but without limitation, heart valves, stents, shunts, filters and other devices positioned within the body.

Figure 2B:
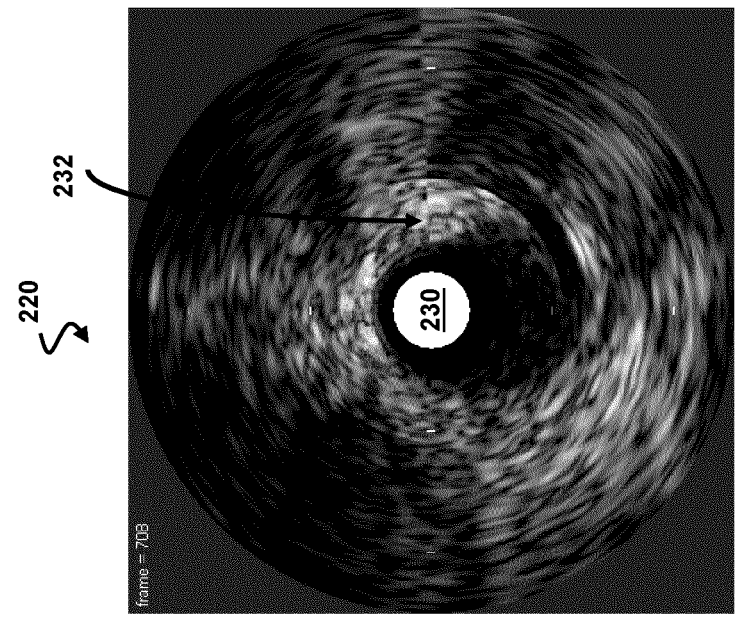
FIG. 2B is a cross-sectional ultrasound image illustrating the effect of ringdown thermal drift under static ringdown subtraction according to embodiments of the present disclosure.
Figure 2A:
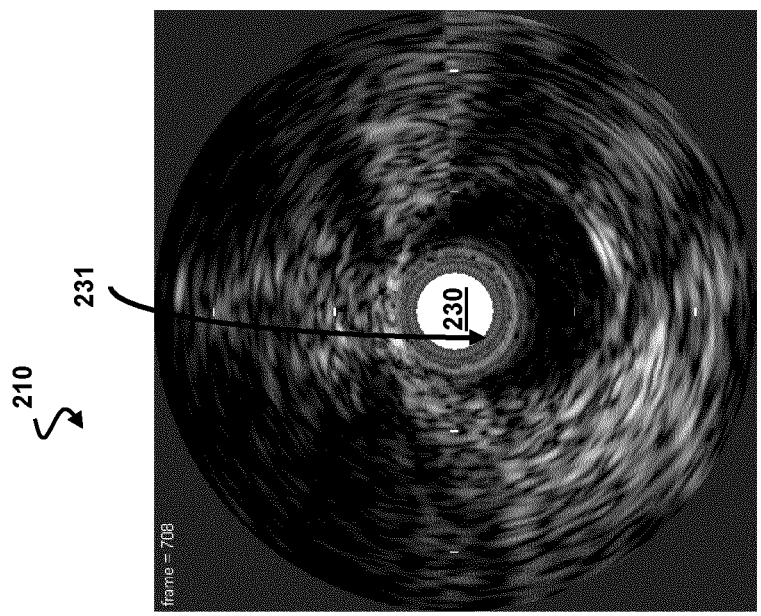
FIG. 2A is a cross-sectional ultrasound image of a vessel including a ringdown artifact component according to embodiments of the disclosure.

FIG. 2A is a cross-sectional ultrasound image 210 of a vessel including a ringdown artifact component 211 according to embodiments of the disclosure. For example, the ultrasound image 210 is produced from the system 100, where the elongate member 102 is placed in the vessel 104 and the transducers 108 emit ultrasonic signal pulses and receive echo signals of the ultrasonic signal pulses reflected by the vessel 104. The ultrasound image 210 is reconstructed from the received echo signals. The ringdown artifact component 211 is located adjacent to a region 230 corresponding to cross-sectional area of the elongate member 102.

As described above, ringdown artifacts can interfere or hide tissues in a region close to a catheter surface. One approach to reducing or removing ringdown artifacts is to obtain a single static reference frame, which is an estimate of a ringdown signal generated by oscillations in transducers, and subtract the reference frame from subsequent image frames. In the static approach, the reference frame is generated or acquired prior to starting the imaging process. For example, the reference frame may be acquired by placing the elongate member 102 in a large vessel to obtain an echo-free waveform. The static approach is limited due to the user interaction required for obtaining the reference frame. In addition, the static approach does not address ringdown thermal drift. Ringdown thermal drift is caused by thermal variation near a transducer and surrounding acoustic medium. The variation can cause drifting in the amplitude and/or the phase of the ringdown signal. The ringdown thermal drift can degrade the quality of the resulting image over time since the reference frame is statically captured prior to the imaging process, and thus does not represent the ringdown signal over time. For example, ringdown thermal drift can cause ghost artifacts or ghost tissues in resulting images. In addition, the static approach does not address other tissue artifact captured while obtaining the echo-free waveform. It is not always possible to obtain a static reference frame in a large vessel free of other structures and therefore ultrasound echoes. As a result, these echoes are captured in the static reference frame and the echoes can cause ghost artifacts and ghost tissues in resulting images.

FIG. 2B is a cross-sectional ultrasound image 220 illustrating the effect of ringdown thermal drift under static ringdown subtraction according to embodiments of the present disclosure. The image 220 is constructed from the same received echo signals as the image 210, but the static ringdown subtraction approach described above is applied to the received echo signals to remove the ringdown component 231. As shown, the ringdown component 231 is removed from the image 220. However, a ghost tissue 232 appears in the image 220 due to ringdown thermal drift.

Figure 2C:
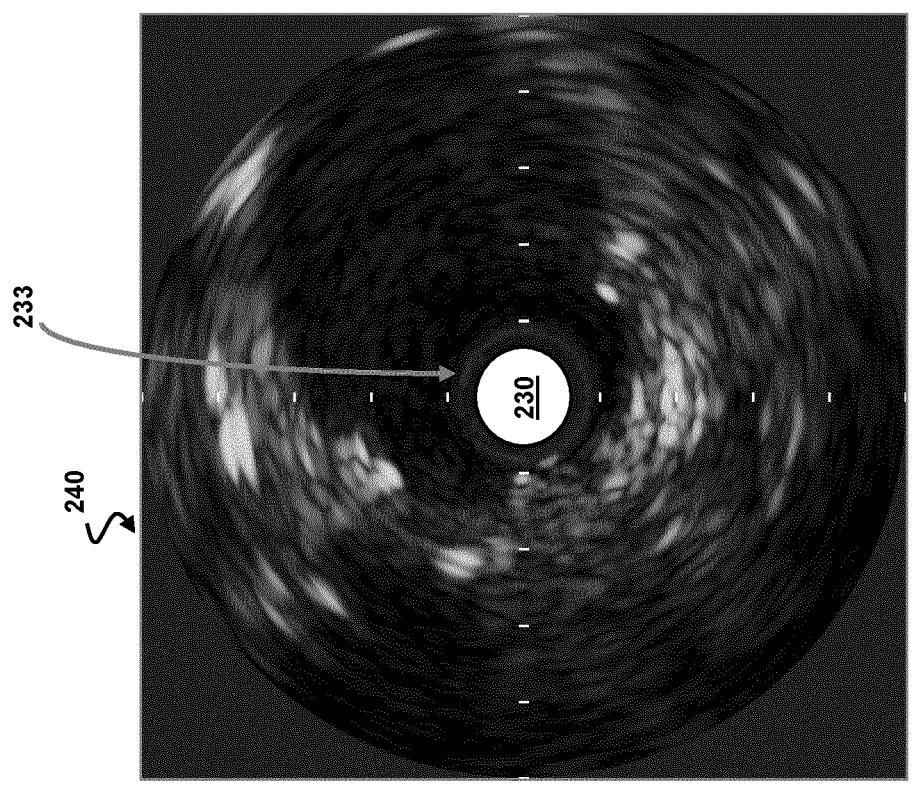
FIG. 2C is a cross-sectional ultrasound image illustrating the effect of ringdown ghost artifacts, due to other tissue structures being captured in a static reference frame, under static ringdown subtraction according to embodiments of the present disclosure.

FIG. 2C is a cross-sectional ultrasound image 240 illustrating the effect of ringdown ghost artifacts, due to other tissue structures being captured in the static reference frame, under static ringdown subtraction according to embodiments of the present disclosure. The image 240 is constructed from the same received echo signals as the image 210, but a different placement in the vessel, and the static ringdown subtraction approach described above is applied to the received echo signals to remove the ringdown component 231 seen in image 210. As shown, the ringdown component 231 is removed from the image 240. However, a ghost tissue 233 appears in the image 240 due to capture of the tissue structure in the static reference frame.

Another approach adaptively updates a reference frame to mitigate the ringdown thermal drift and eliminate the need to acquire the ringdown reference frame prior to the imaging process. In the adaptive approach, the reference frame is updated based on an average of several frames. The adaptive approach operates based on the assumption that ringdown artifacts vary slowly or almost constant across time, whereas vessel motions vary substantially from frame to frame. Thus, the averaging can provide a good estimate of the ringdown artifacts. The adaptive approach may perform well when the reference frame is updated at a faster rate than the ringdown thermal drift, and when the reference frame is updated slower than the tissue structure motion. However, the performance can degrade when used for measurements in small coronary vessels, peripheral vessels, and or under signal saturation conditions. For example, when a catheter is wedged in a small vessel, tissue motions are lessened or restricted. Under a signal saturation condition, such as if certain structures like stents or calcification in tissue structures is present, the changes in signal amplitudes and/or phases are not detectable. Peripheral vessels have less vessel motions than coronary vessels due to the cardiac cycle pressure wave changes and the lessened curvatures in the peripheral vessels. When tissue motions are reduced or undetectable, the adaptive approach may introduce tissue information from a previous frame into a current frame, causing similar ghost artifacts as shown in the image 220. Thus, both the static ringdown subtraction and the adaptive ringdown subtraction may not be effective in removing ringdown artifacts.

Disclosed herein are various embodiments of an improved ringdown reduction system. The disclosed embodiments automatically initiate an adaptive ringdown subtraction process upon receiving imaging data. The ringdown subtraction process performs IIR averaging to adaptively estimate ringdown and subtracts the ringdown estimate from the imaging data. The disclosed embodiments perform data selection and masking on the imaging data and the ringdown-subtracted data to identify ringdown from slow-moving tissues and fast-moving tissues. Thus, the disclosed embodiments are suitable for use with coronary vessels and peripheral vessels. In addition, the data selection and masking minimizes subtraction of information of stationary tissues and is robust to signal saturation. Thus, the performance is not degraded when tissues are wedged in a tight vessel or when the system is under signal saturation. For example, the disclosed embodiments can identify and remove ringdown when tissues are at a distance of about 100 microns away from a catheter surface. Further, the data selection and masking can reduce or remove ghost artifacts or ghost tissues carry from a previous image frame into a current image frame. Thus, the disclosed embodiments can reduce or avoid mis-intepretation or mis-measurement of tissue structures. Although the disclosed embodiments are described in the context of ringdown artifacts of phased array devices, the disclosed embodiments are suitable for use in removing halo artifacts of rotational devices. In addition, the disclosed embodiments can be used in conjunction with a manual initiation of the ringdown subtraction process and any suitable type of averaging for acquiring the ringdown estimate.

Figure 4:
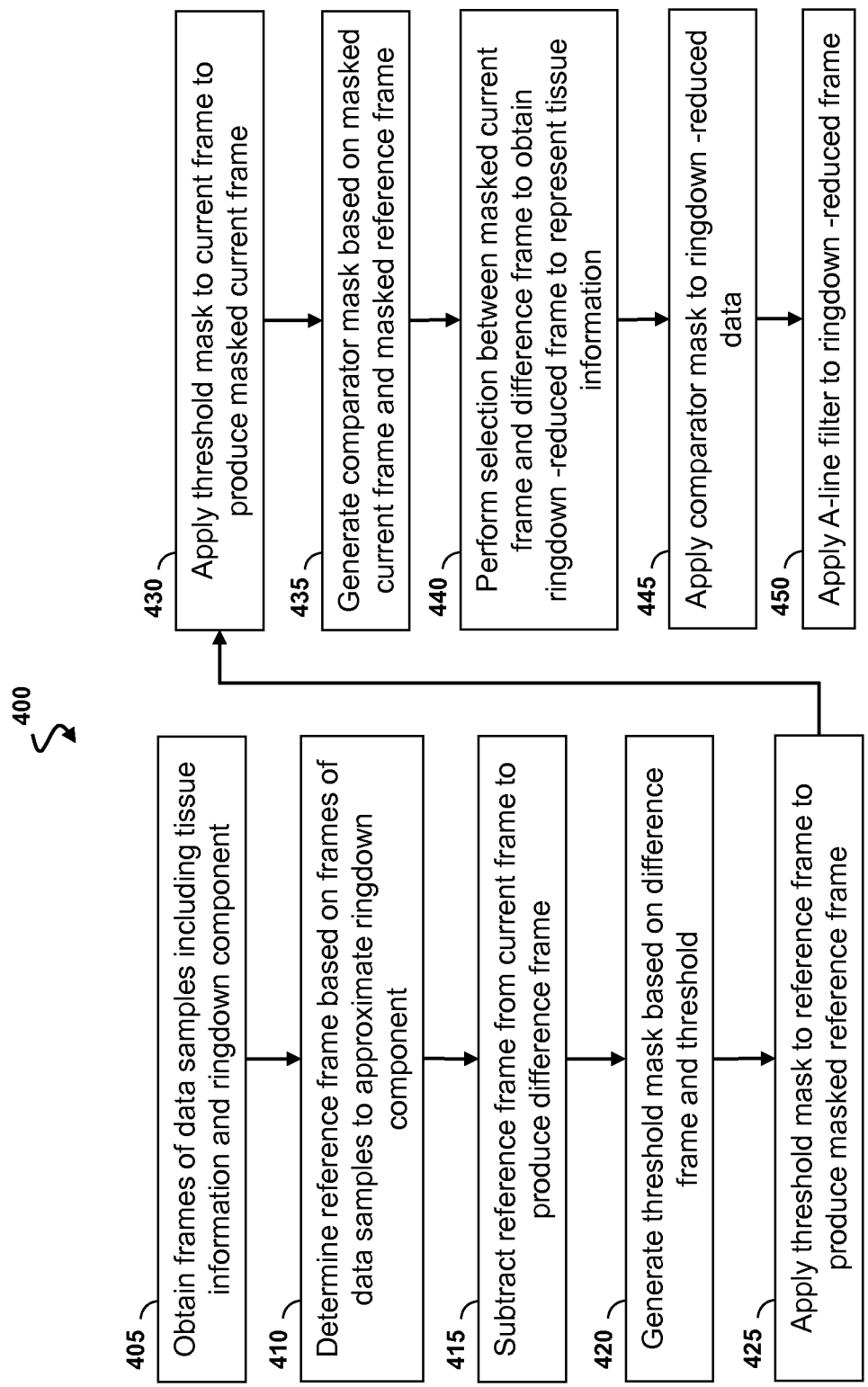
FIG. 4 is a flow diagram of a method of correcting ringdown-distorted imaging data according to embodiments of the present disclosure.

A method of processing ultrasound imaging data is described with reference to FIGS. 3-8. FIG. 3 is a flow diagram of a method 300 of processing ultrasound imaging data according to embodiments of the present disclosure. It is understood that additional steps can be provided before, during, and after the steps of method 300, and that some of the steps described can be replaced or eliminated for other embodiments of the method. FIG. 4 is a flow diagram of a method 400 of correcting ringdown-distorted imaging data according to embodiments of the present disclosure. It is understood that additional steps can be provided before, during, and after the steps of method 400, and that some of the steps described can be replaced or eliminated for other embodiments of the method. The steps of the methods 300 and 400 can be implemented by an ultrasound image processing system such as the IVUS processing system 114 and the ultrasound image processing system 500 or any other suitable system, device, or component that are coupled to the elongate member 102, which may be a direct coupling or via the PIM 112. The methods 300 and 400 are implemented after placing the elongate member 102 into the vessel 104 and configuring the transducers 108 to transmit ultrasound signal pulses.

Figure 5:
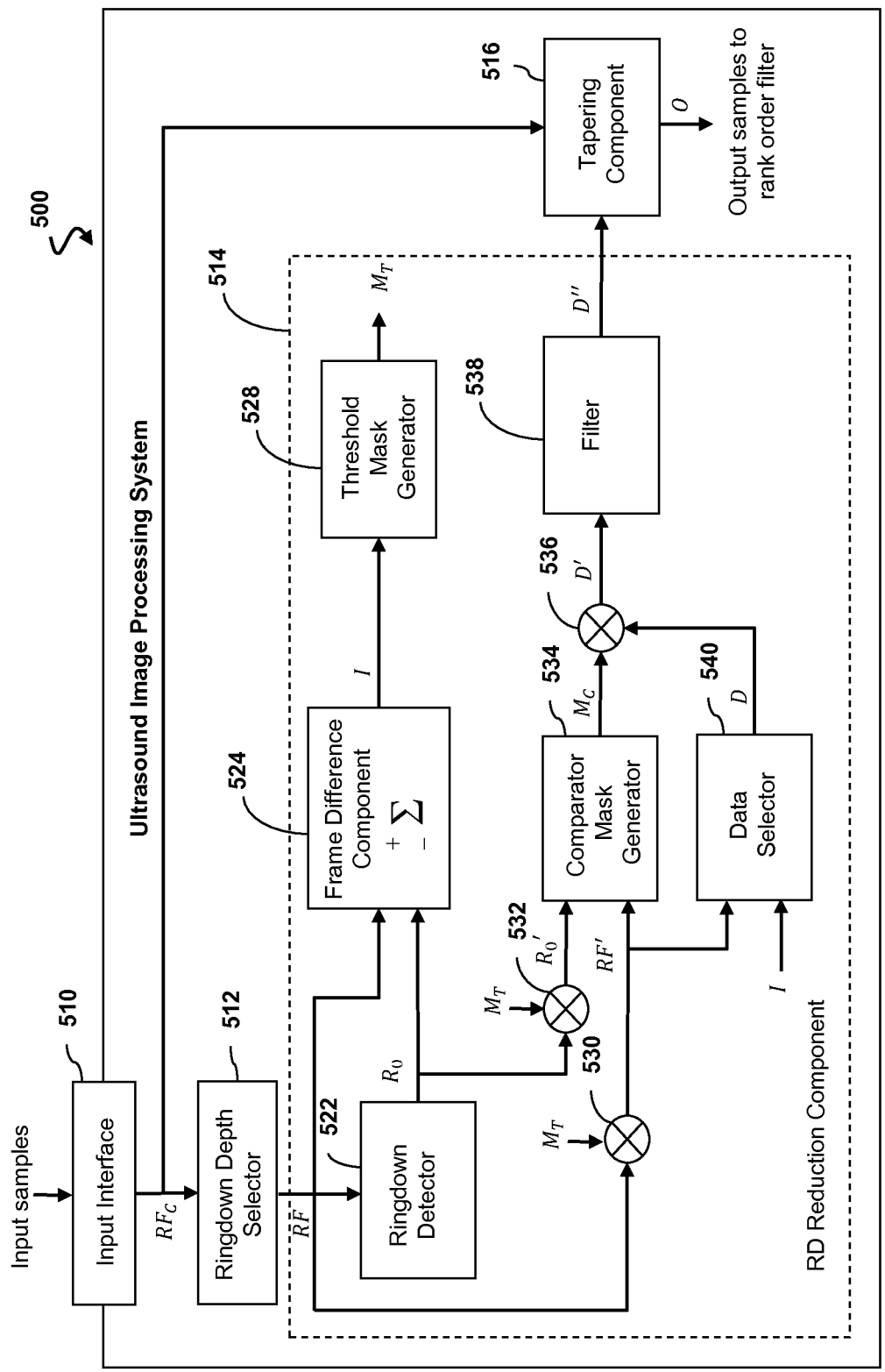
FIG. 5 is a schematic diagram of an ultrasound image processing system according to embodiments of the present disclosure.

FIG. 5 is a schematic diagram of an ultrasound image processing system 500 according to embodiments of the present disclosure. The system 500 may be incorporated into an IVUS processing system 114 and/or other components of an imaging system 100. The system 500 may include an input interface 510, a ringdown depth selector 512, a ringdown reduction component 514, and a tapering component 516. The ringdown reduction component 514 includes a ringdown detector 522, a frame difference component 524, a threshold mask generator 528, a comparator mask generator 534, a data selector 540, multiplication components 530, 532, and 536, and a filter 538. The components of the system 500 can be implemented as hardware components and/or software components executed on one or more central processing units (CPUs), general purpose processors, digital signal processors (DSPs), application-specific integrated circuits (ASICs), and/or functional programmable gated arrays (FPGA).

Referring to the step 305 of the method 300 and FIG. 5, in an embodiment, a plurality of complete frames of samples including tissue information and a ringdown component is received. The ringdown component can be similar to the ringdown component 231 shown in the image 220. The plurality of complete frames is received by the input interface 510 of the system 500. The samples correspond to echo signals of the transmitted ultrasound signal pulses reflected from the tissues under the imaging process. The transducers 108 receive the echo signals and the control circuitry 110 transfers the received echo signals to the input interface 510, for example, via the PIM 112. A complete frame of samples refers to samples collected from a field-of-view (FOV) of the transducers 108. The samples are sample points of A-lines. The samples carry amplitude and phase information of the received echo signals. For example, an $i^{th}$ sample point of a $j^{th}$ A-line can be represented as $RF_C(i,j)$. A-lines refer to the echo signal received from groupings of emitting and receiving transducers. Any emitting transducer and any receiving transducer may be configured together to form a transmit-receive pair, and the echo received from this is an A-line. Within an A-line, more than one emitting transducer and more than one receiving transducer may be configured to act together. In some embodiments, a transducer may be designated as both an emitting and a receiving transducer.

Referring to the step 310 of the method 300 and FIG. 5, in an embodiment, portions of the plurality of complete frames of data samples are selected based on a ringdown depth to produce a plurality of frame segments of data samples. The frame segments are selected by the ringdown depth selector 512. The ringdown depth selector 512 receives the complete frames from the input interface 510 and selects a portion of the data samples from each complete frame corresponding to a ringdown region to form a frame segment of data samples, denoted as $RF(i,j)$, where i, j represents an $i^{th}$ sample point of a $j^{th}$ A-line, as shown below:

$$RF(i,j)=RF_C(i,j), \text{ for } i<\text{ringdown depth.} \quad (1)$$

The ringdown depth may vary in different embodiments depending on the characteristics of the transducers 108 and the elongate member 102. The ringdown depth selector 512 may consider the entire data set, rather than a sub-region of the data set (e.g., ringdown_depth=entire Field-of-View (FOV) as acquired in the received ultrasound echo data). For example, a complete frame may include 1024 samples per A-line and the ringdown depth selector 512 may select the first 256 samples corresponding to a region near the surfaces of the transducers 108 for each A-line. In other embodiments, the ringdown depth selector 512 may set the ringdown depth to 1024 samples, thereby allowing the entire complete frame to be processed.

Referring to the step 315 of the method 300 and FIG. 5, in an embodiment, the plurality of frame segments of data samples are processed to produce a ringdown-reduced frame. The frame segments are processed by the ringdown reduction component 514. The ringdown reduction component 514 receives the frame segments from the ringdown depth selector 512. The ringdown reduction component 514 processes each frame segment by selecting tissue information and discarding ringdown components to produce a ringdown-reduced frame, as described in greater detail herein. For example, the step 315 can implement the method 400.

Referring to the step 320 of the method 300 and FIG. 5, in an embodiment, a tapering function is applied to the ringdown-reduced frame and a corresponding complete frame to produce an ultrasound image. The tapering function is applied by the tapering component 516. The tapering component 516 receives ringdown-reduced frames from the ringdown reduction component 514 and combines each ringdown-reduced frame with the corresponding complete frame to produce an ultrasound image, which is a corrected complete frame, denoted as O, for each complete frame. The tapering function provides a smooth transition between the ringdown-reduced frame and the corresponding complete frame, as described in greater detail herein. In some embodiments, when the ringdown-reduced frame is the same as the complete frame, then the taper function is not used.

The method 400 processes ringdown-distorted imaging data by selecting tissue information and removing ringdown components from the ringdown-distorted data. The method 400 is described in the context of processing a current frame and can be repeated to process subsequent frames. Referring to the step 405 of the method 400 and FIG. 5, in an embodiment, a plurality of frames of data samples including tissue information and a ringdown component is obtained. The plurality of frames may correspond to the frame segments produced within the range of ringdown in the step 310 of the method 300 or complete frames corresponding to a FOV. A current frame of the plurality of frames is denoted as RF.

Referring to the step 410 of the method 400 and FIG. 5, in an embodiment, a reference frame is determined based on the plurality of frames of samples to approximate the ringdown component. The reference frame is determined by the ringdown detector 522. The ringdown detector 522 receives the frames from the ringdown depth selector 512 and determines the reference frame by applying an averaging function to the plurality of frames. As described above, ringdown varies slowly or almost constant in time compared to tissue motions. Thus, the averaging can remove the effect of the tissue motions and provide an estimate of the ringdown component. The averaging function can be based on a weighted sum, a finite impulse response (FIR) average, an infinite impulse response (IIR) average, or any suitable averaging scheme. The averaging function enables automatic update of the reference frame to adapt to ringdown variations such as thermal drift. The IIR averaging is a recursive update, which computes a weighted sum of a current frame and a previous frame. The IIR averaging can provide a fast update of the reference frame. In addition, averaging may include a threshold function to exclude certain signal ranges from the average, such as very small or very large signals. A basic IIR averaging scheme without a threshold function and a piecewise-update IIR averaging scheme are described in greater detail herein. The reference frame is denoted as $R_0$.

Referring to the step 415 of the method 400 and FIG. 5, in an embodiment, the reference frame is subtracted from a current frame of the plurality of frames to produce a difference frame. The subtraction is performed by the frame difference component 524. The frame difference component 524 receives the reference frame and the current frame from the ringdown detector 522 and the ringdown depth selector 512, respectively. The frame difference component 524 operates on each sample as shown below:

$$I(i,j)=RF(i,j)-R_0(i,j), \quad (2)$$

where $RF(i,j)$ represents an $i^{th}$ sample point of a $j^{th}$ A-line in the current frame, $R_0(i,j)$ represents an $i^{th}$ sample point of a $j^{th}$ A-line in the reference frame, $I(i,j)$ represents an $i^{th}$ sample point of a $j^{th}$ A-line in the difference frame. The subtraction can remove most of the ringdown component from the current frame. However, the difference frame can include tissue information of a previous frame since the reference frame is an average of the current frame and the previous frame. In addition, the difference frame may include ringdown residuals, such as PZT noise and fast thermal drifts. Thus, additional processing is required to identify tissue information of the current frame.

In some embodiments, the frame difference component 524 can optionally perform a clipping function to prevent overflow due to a dynamic range of the system 500 as shown below:

If $I(i,j)$>maximum value, then $I(i,j)$=maximum value.

If $I(i,j)$<minimum value, then $I(i,j)$=minimum value. (3)

The clipping limits the magnitudes of the samples in the difference frame to be within the maximum value and the minimum value of the system 500.

Referring to the step 420 of the method 400 and FIG. 5, in an embodiment, a threshold mask is generated based on the difference frame and a threshold. The threshold mask is generated by the threshold mask generator 528. The threshold mask generator 528 receives the difference frame from the frame difference component 524 and generates the threshold mask as shown below:

If $|I(i,j)|<T$ then $M_T(i,j)=0$, else $M_T(i,j)=1$, (4)

where $|I(i,j)|$ represents the absolute magnitude of I(i,j), $M_T$ represents the threshold mask, and T represents the threshold. The threshold can be any suitable value. In an embodiment, T is set to a value of about 1. Thus, equation (4) sets any non-zero valued sample to a value of 1.

Referring to the step 425 of the method 400 and FIG. 5, in an embodiment, the threshold mask is applied to the reference frame to produce a masked reference frame. Referring to the step 430 of the method 400 and FIG. 5, in an embodiment, the threshold mask is applied to the current frame to produce a masked current frame. The applying of the generator mask to the reference frame and the current frame is performed by the multiplication components 532 and 530, respectively, but can alternatively be performed by a MUX operation since the mask includes values of ones and zeros, which is a conditional logic. The applying of the generator mask to the reference frame and the current frame suppresses ringdown residuals. The masked reference frame is denoted as $R_0'$. The masked current frame is denoted as RF'. A higher threshold T can be used to further reduce ringdown residuals, but may degrade tissue information. In some embodiments, instead of generating the generator mask and applying the generator mask as shown in FIG. 5, ringdown residual can be suppressed by setting the lower significant bits of the samples in the reference frame to bit values of zeros prior to subtracting the reference frame from the current frame.

In addition, the threshold mask generator 528 can alternatively be used to exclude larger signals, for example, by setting the higher significant bits of the samples in the reference frame to bit values of zeros prior to subtracting the reference frame from the current frame. This can remove deleterious components in the ringdown reference which are not ringdown residual but instead may be caused by defects in catheter manufacturing process such as excessive glue on the catheter in front of the transducer elements. In other embodiments the threshold mask generator could include a weighting function to establish the mask. The weighting function could be a range based taper, applied to signal I, and then compared to a threshold.

Referring to the step 435 of the method 400 and FIG. 5, in an embodiment, a comparator mask is generated based on the current frame and the difference frame. The comparator mask is generated by the comparator mask generator 534. The comparator mask generator 534 receives the masked reference frame and the masked current frame and generates the comparator mask as shown below:

If $|RF'(i,j)|\geq|R_0'(i,j)|$ then $M_C(i,j)=1$, else $M_C(i,j)=0$, (5)

where $|RF'(i,j)|$ represents the absolute magnitude of a sample in the masked current frame, $|R_0'(i,j)|$ represents the absolute magnitude of a sample in the masked reference frame, C is a scale factor, and $M_C$ represents the comparator mask. The area under the comparator mask that has values of ones indicates a high probability of tissue information of the current frame in the area. However, the area can also include tissue information of a previous frame. The comparator mask can be improved by scaling the masked reference frame as shown below:

If $|RF'(i, j)| \geq \dfrac{|R_0'(i, j)|}{C}$ (6)

then $M_C(i, j) = 1$, else $M_C(i, j) = 0$, where C represents a comparator mask scale factor. The comparator mask scale factor C can be set to any suitable value. In an embodiment, C is set to a value of about 2. In other embodiments the comparator mask generator 534 can be alternatively configured with a weighting function to establish the mask, instead of utilization of a fixed threshold. The weighting function could be a fuzzy weighting, controlled by the signal strength present in the signals $|RF'(i,j)|$ and $|R_0'(i,j)|$.

Referring to the step 440 of the method 400 and FIG. 5, in an embodiment, a selection is performed between the masked current frame and the difference frame to obtain a ringdown-reduced frame to represent the tissue information. The selection is performed by the data selector 540. The data selector 540 receives the masked reference frame from the multiplication component 530 and the difference frame from the frame difference component 524. The data selector 540 performs the selection as shown below:

If $|RF'(i,j)|<|I(i,j)|$ then $D(i,j)=RF'(i,j)$, else $D(i,j)=I(i,j)$, (7)

where D represents the ringdown-reduced frame. Since the current frame includes tissue information of the current frame but also the ringdown artifact, and the difference frame includes tissue information of both the current frame and any captured tissue information in the reference frame, the selection is performed to exclude tissue information of the reference frame from the ringdown-reduced frame. Since the current frame includes the ringdown artifact, and the difference frame does not, it is ensured that the ringdown artifact from the current frame is not included in the output D(i,j).

Referring to the step 445 of the method 400 and FIG. 5, in an embodiment, the comparator mask is applied to the ringdown-reduced frame. The applying of the comparator mask is performed by the multiplication component 536, but can alternatively be performed by a MUX operation since the mask includes values of ones and zeros, which is a conditional logic. The masked ringdown-reduced frame is denoted as D'. As described above, the area of the comparator mask that has values of ones indicate a high probability of tissue information in the current frame. Thus, the applying of the comparator mask further limits the selection performed by the step 440. After the selection and the comparator mask operations, the masked ringdown-reduced frame includes the tissue information of the current frame and a minimal amount or close to zero amount of ringdown residual.

Referring to the step 450 of the method 400 and FIG. 5, in an embodiment, the filter 538 is applied to the masked ringdown-reduced frame. The filtered ringdown-reduced frame is denoted as D″. The filtering can smooth out discontinuities caused by the masking and selection operations. The filter 538 can be FIR, IIR, or a moving average window. When the filter 538 is a FIR, the filter 538 can have any suitable number of taps. In one embodiment, the filter 538 is an A-line filter filtering samples across angles or A-lines. In another embodiment, the filter 538 can filter across samples within A-lines instead of filtering samples across angles or A-lines. After computing the filtered ringdown-reduced frame, the filter ringdown-reduced frame can be combined with the complete image as described in the step 320 and with greater detail herein.

Figure 6:
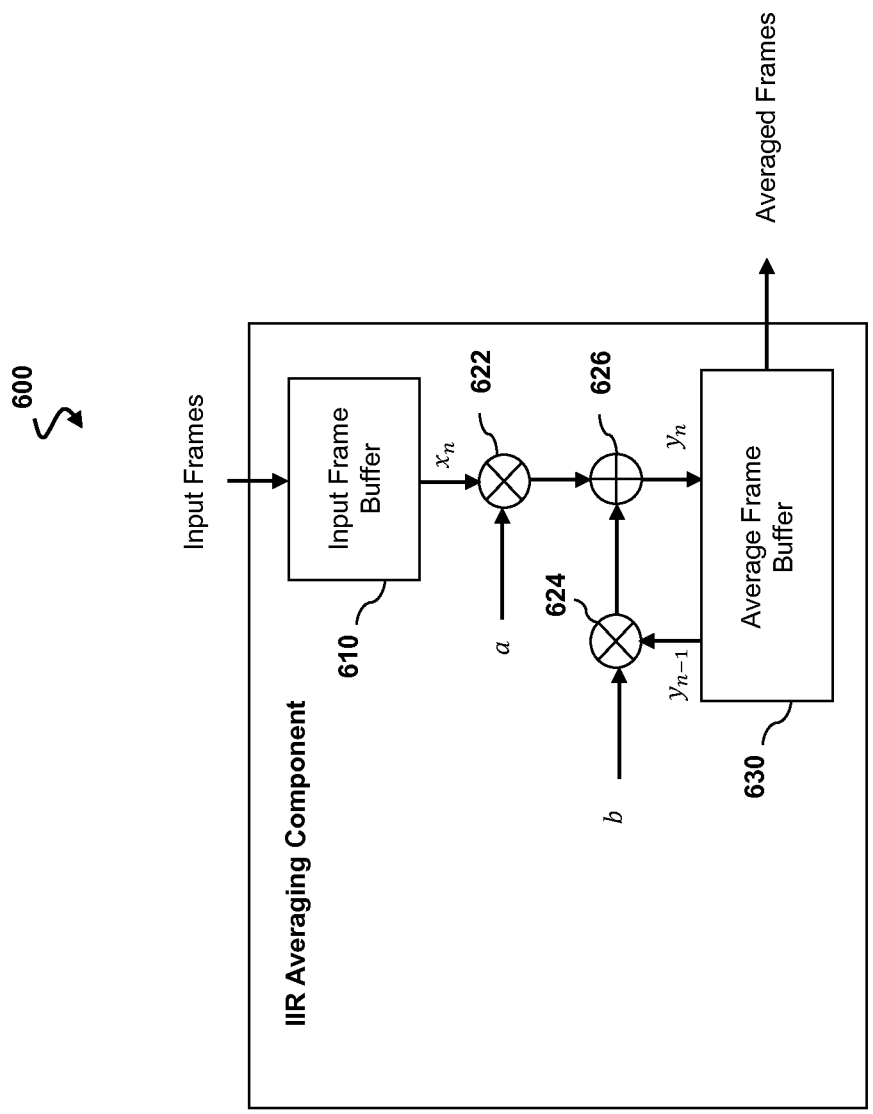
FIG. 6 is a schematic diagram of an infinite impulse response (IIR) averaging component according to embodiments of the present disclosure.

FIG. 6 is a schematic diagram of an IIR averaging component 600 according to embodiments of the present disclosure. The IIR averaging component 600 can be incorporated into the ringdown detector 522 and can be implemented by the step 410 of the method 400. The IIR averaging component 600 includes an input frame buffer 610, multiplication components 622 and 624, a summing component 626, and an average frame buffer 630. The IIR averaging component 600 perform averaging by computing a weight sum of a current frame and a previous averaged frame. The multiplication component 622 multiples a current frame, denoted as x, obtained from the input frame buffer 610 with a current frame coefficient, denoted as a. The multiplication component 624 multiples a previous averaged frame, denoted as $y_{n-1}$, obtained from the average frame buffer 630 with a previous frame coefficient, denoted as b. The summing component 626 sums the weighted current frame and the weighted previous averaged frame and saves the sum to the average frame buffer 630. The input frame buffer 610 and the average frame buffer 630 can arrange input frames and averaged frames in any suitable configuration. The IIR averaging component 600 operates on each sample as shown below:

$$y_n(k) = a \times x_n(k) + b \times y_{n-1}(k), \tag{8}$$

where $x_n(k)$ represents a $k^{th}$ sample of the current frame, $y_{n-1}(k)$ represents a $k^{th}$ sample of the previous averaged frame, and $y_n(k)$ represents a $k^{th}$ sample of the current averaged frame. For example, when the IIR averaging component 600 is incorporated into the ringdown detector 522, $x_n(k)$ and $y_n(k)$ correspond to RF(i,j) and $R_O$ (i,j), respectively. In an embodiment, the current frame coefficient and the previous frame coefficient are fractional coefficients that sum up to 1. In some embodiments, the fractional current frame coefficient and the fractional previous frame coefficient can be adjusted to control an update rate of the IIR averaging component 600. The adjustment can change a ratio between the fractional current frame coefficient and the fractional previous frame coefficient such that a sum of the fractional current frame coefficient and the fractional previous frame coefficient remains at a value of 1.

Figure 7:
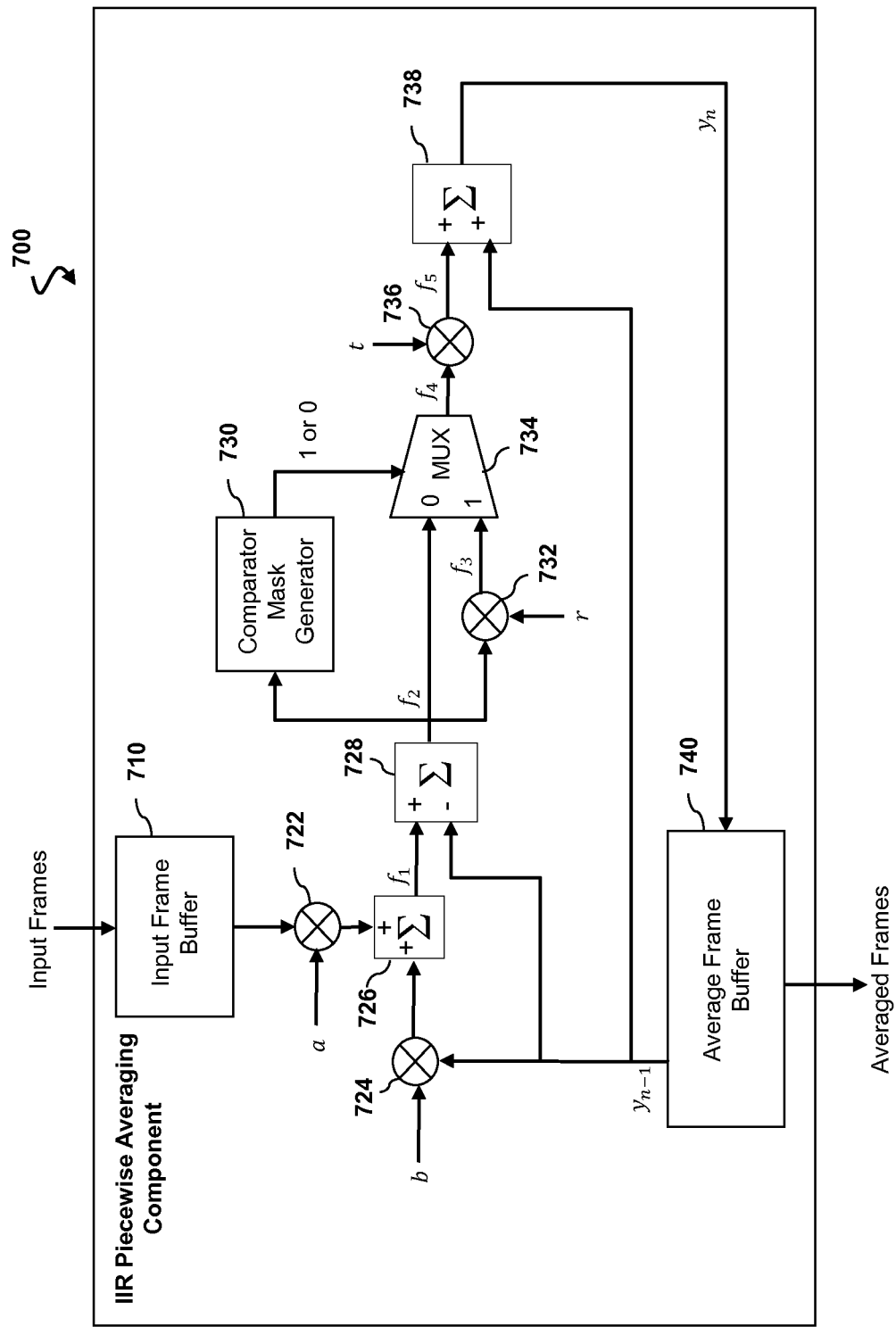
FIG. 7 is a schematic diagram of an IIR averaging component that implements piecewise update according to embodiments of the present disclosure.

FIG. 7 is a schematic diagram an IIR averaging component 700 that implements piecewise update according to embodiments of the present disclosure. The IIR averaging component 700 can be incorporated into the ringdown detector 522 and can be implemented by the step 410 of the method 400. The IIR averaging component 700 performs similar IIR averaging as the IIR averaging component 600, but adjusts the update rate of the IIR averaging. The IIR averaging component 700 includes an input frame buffer 710, multiplication components 722, 724, 732, and 736, summing components 726 and 738, a subtraction component 728, a comparator mask generator 730, multiplexers (MUXs) 734 and 740, and an average frame buffer 750.

The multiplication component 722 multiples a current frame, denoted as x, obtained from the input frame buffer 710 with a current frame coefficient, denoted as a. The multiplication component 724 multiples a previous averaged frame, denoted as $y_{n-1}$, obtained from the average frame buffer 750 with a previous frame coefficient, denoted as b. The summing component 726 sums the weighted current frame and the weighted previous averaged frame to produce a first frame, denoted as $f_1$, as shown below:

$$f_1(k) = a \times x_n(k) + b \times y_{n-1}(k), \tag{9}$$

where $x_n(k)$ represents a $k^{th}$ sample of the current frame, $y_{n-1}(k)$ represents a $k^{th}$ sample of the previous averaged frame, and $f_1(k)$ represents a $k^{th}$ sample of the first frame current averaged frame.

Instead of using the first frame to update the previous averaged frame to the current averaged frame, the IIR averaging component 700 uses a portion of the first frame for the update to slow down the update. To control an update rate, the subtraction component 728 subtracts the previous averaged frame $y_{n-1}$ from the first frame to produce a second frame, denoted as $f_2$, and the multiplication component 732 multiplies the second frame with a rate limit factor, denoted as r, to produce a third frame, denoted as $f_3$, as shown below:

$$f_2(k) = f_1(k) - y_{n-1}(k)$$

$$f_3(k) = r \times f_2(k), \tag{10}$$

where $f_2(k)$ represents a $k^{th}$ sample of the second frame and $f_3(k)$ represents a $k^{th}$ sample of the third frame. The third frame represents a portion of a difference between the computed averaged frame or the first frame and the previous averaged frame.

The IIR averaging component 700 can further slow down the update by using a snap function to reuse the previous averaged frame as a current averaged frame when the difference between the computed averaged frame and the previous averaged frame is small. The comparator mask generator 730 implements the snap function as shown below:

If $f_1(k) > T_S$ then $M_S(k) = 1$, else $M_S(k) = 0$, (11)

where $M_S(k)$ represents a $k^{th}$ sample of the comparator mask and $T_S$ is a snap threshold. The snap threshold can be any suitable value. In an embodiment, the snap threshold is set to a value of about 8. The MUX 734 selects a $k^{th}$ sample from the third frame when $M_S(k)$ is 1, otherwise selects a $k^{th}$ sample from the first frame to produce a fourth frame.

After determining an update portion for the current averaged frame, the multiplication component 736 multiples the fourth frame by a tapering factor, denoted as t, to produce a fifth frame, denoted as $f_5$, and the summing component 738 sums the fifth frame and the previous averaged frame to produce a current averaged frame, denoted as $y_n$, as shown below:

$$f_5(k) = t \times f_4(k)$$

$$y_n(k) = f_5(k) + y_{n-1}(k), \tag{12}$$

where $f_5(k)$ represents a $k^{th}$ sample of the fifth frame and $y_n(k)$ represents a $k^{th}$ sample of the update frame. The tapering factor can be any suitable value. In an embodiment the tapering factor changes with range (sample position), thereby modifying the update rate according to range. The rate limit factor r, the tapering factor t, and the snap threshold $T_S$ can be adjusted to control an update rate of the BR averaging. In an embodiment, the rate limit factor r, the tapering factor t, and the snap threshold $T_S$ can be determined based on the catheter in use and can be pre-calibrated to set to suitable values.

When the IIR averaging component 700 is incorporated into the ringdown detector 522, $x_n(k)$ and $y_n(k)$ correspond to $RF(i,j)$ and $R_0(i,j)$, respectively. The use of piecewise update allows the ringdown detector 522 to control the update rate of the averaging over a greater range of update rate than the IIR averaging could alone. As described above, BR averaging can provide a fast update. For example, the IIR averaging can provide a full update in about 3 frames, which may be faster than variations in tissue motions. Thus, tissues in resulting images may appear with an undesirable shimmering or stroboscopic effect. The controlling of the rate limit factor r, the tapering factor t, and the snap threshold $T_S$ can remove or prevent the undesirable effect.

Figure 8:
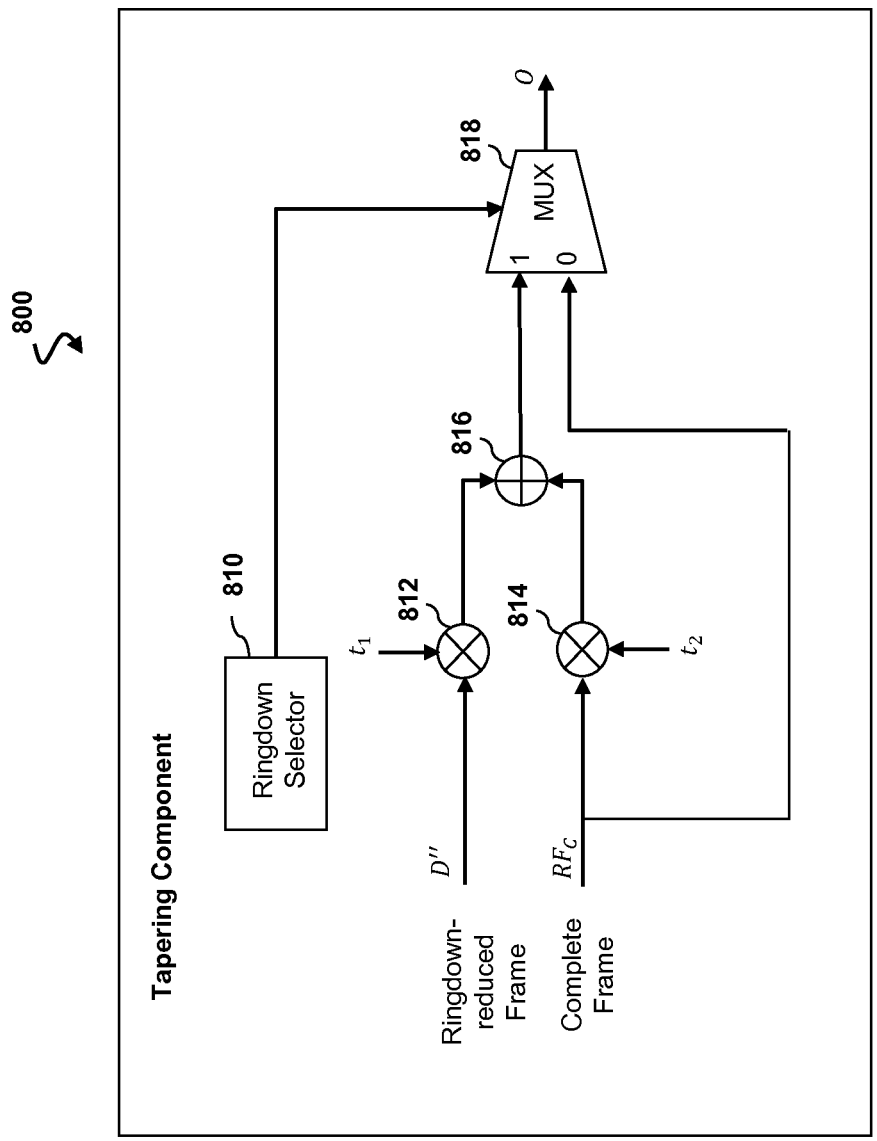
FIG. 8 is a schematic diagram of a tapering component according to embodiments of the present disclosure.

FIG. 8 is a schematic diagram a tapering component 800 according to embodiments of the present disclosure. The tapering component 800 can be incorporated into the tapering component 516. The tapering component 800 includes a ringdown selector 810, multiplication components 812 and 814, a summing component 816, and a MUX 818. The tapering component 800 is used to combine a ringdown-reduced frame produced by the ringdown reduction component 514 with an original complete frame received from the input interface 510. The tapering component 800 can provide a smooth transition during the combining. The multiplication component 812 multiples the filtered ringdown-reduce frame by a first tapering factor, denoted as $t_1$, to produce a tapered ringdown-reduced frame. The multiplication component 814 multiples a corresponding complete frame $RF_C$ received from the input interface 510 by a second tapering factor, denoted as $t_2$, to produce a tapered complete frame. The summing component 816 sums the tapered ringdown-reduced frame and the tapered complete frame to produce a combined frame, denoted as U. The tapering operations are shown below:

$$U(i,j)=t_1 \times D''(i,j)+t_2 \times RF_C(i,j), \qquad (13)$$

In an embodiment, the first tapering factor and the second tapering factor are fractional values that sum up to 1.

The ringdown selector 810 outputs a value of 1 for a ringdown region corresponding to the ringdown-reduced frame, otherwise a value of 0, for example, based on the selection at the ringdown depth selector 512. The MUX 818 multiplexes a portion of the combined frame corresponding to the ringdown region and a portion of the complete frame outside the ringdown region to produce an output frame, denoted as O. The multiplexing operations are shown below:

If $i<RD$ depth then $O(i,j)=D''(i,j)$, else $O(i,j)=RF_C(i,j)$, (14)

where $O(i,j)$ represents an $i^{th}$ sample of a $i^{th}$ A-line.

Figure 9:
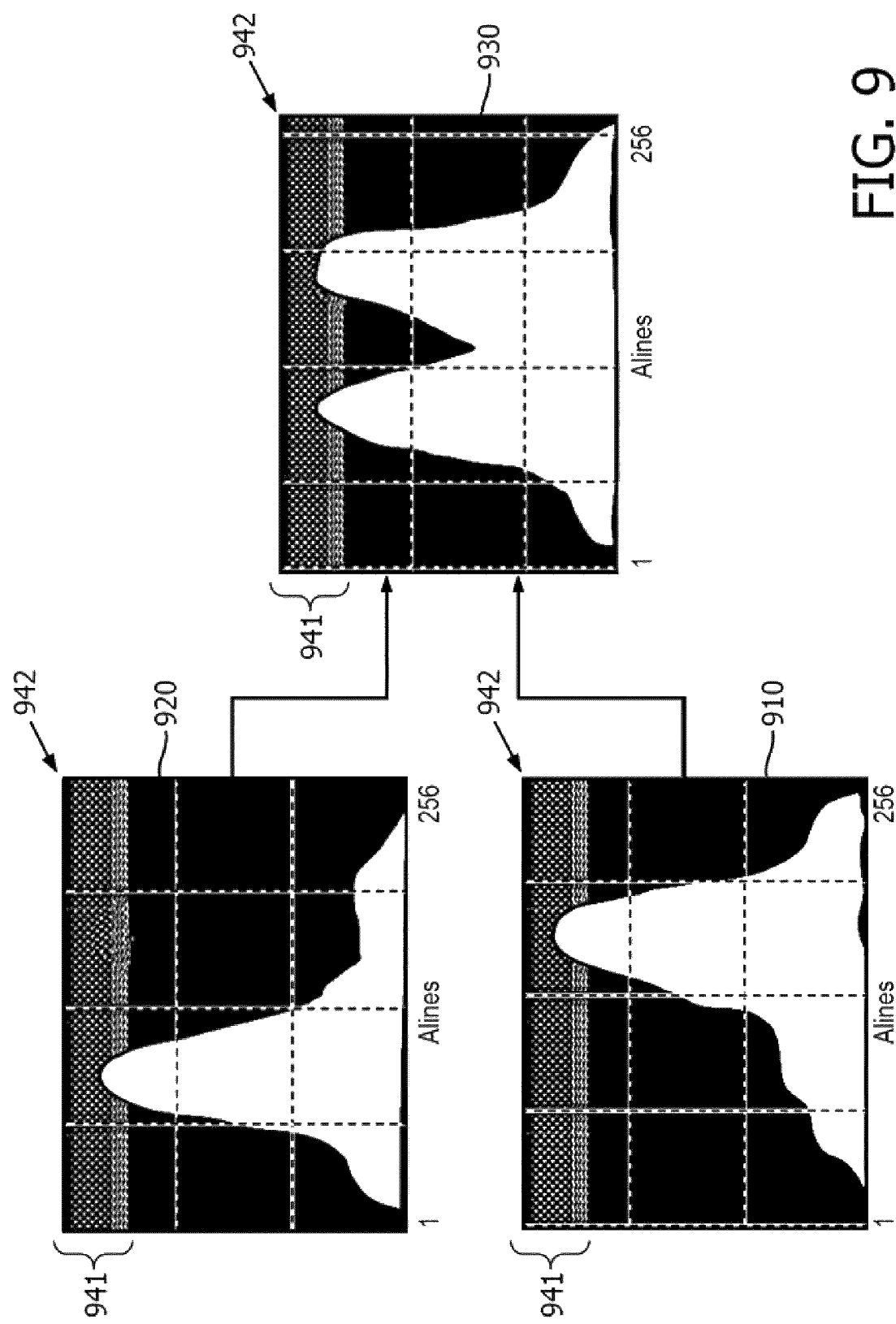
FIG. 9 illustrates a current frame, a reference frame, and a difference frame in a stage of ringdown reduction according to embodiments of the present disclosure.

FIGS. 9-16 collectively illustrate imaging frames at various stages of the ringdown reduction process described above with reference to FIGS. 3-8. In FIGS. 9-17, the x-axis represents A-lines and the y-axis represents samples. FIG. 9 illustrates a current frame 910, a reference frame 920, and a difference frame 930 in a stage of ringdown reduction according to embodiments of the present disclosure. The current frame 910 corresponds to a current frame RF at the output of the ringdown depth selector 512. The reference frame 920 corresponds to a reference frame $R_0$ at the output of the ringdown detector 522. The difference frame 930 corresponds to a difference frame I at the output of the frame difference component 524. The difference frame 930 is a difference between the current frame 910 and the reference frame 920. Each of the current frame 910, the reference frame 920, and the difference frame 930 include a ringdown region 941 adjacent to a catheter surface region 942. The ringdown distortion is shown as a band in the region 941.

Figure 10:
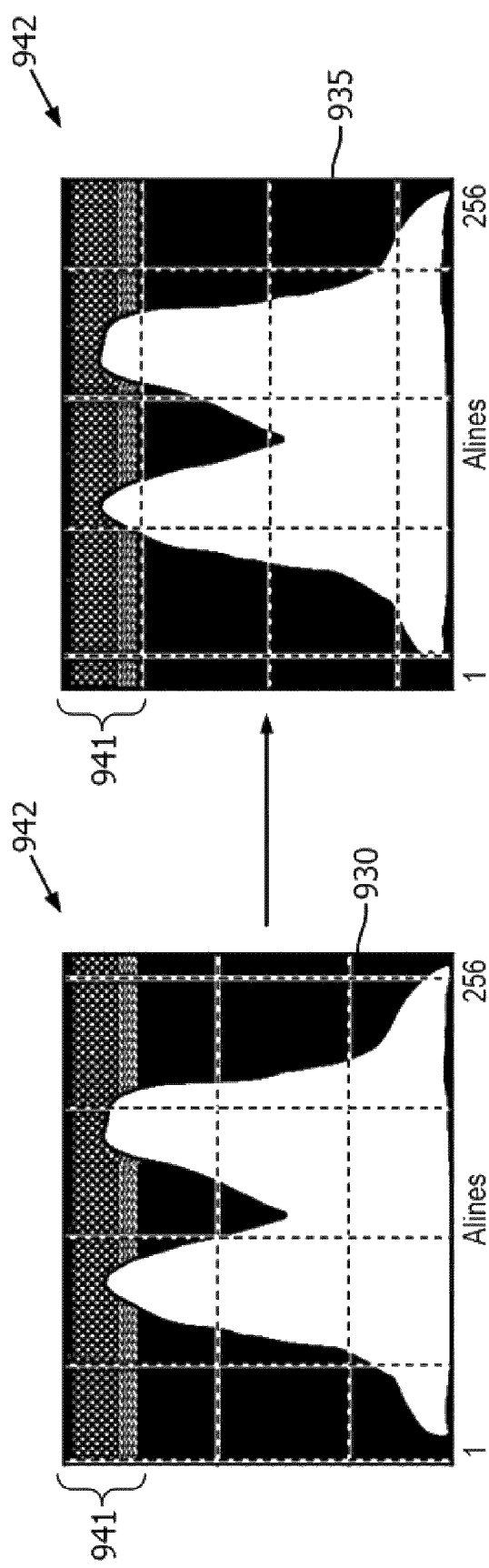
FIG. 10 illustrates a difference frame and a threshold mask in a stage of ringdown reduction according to embodiments of the present disclosure.

FIG. 10 illustrates the difference frame 930 and a threshold mask 935 in a stage of ringdown reduction according to embodiments of the present disclosure. The threshold mask 935 corresponds to a threshold mask $M_T$ at the output of the threshold mask generator 528. The threshold mask 935 is generated from the difference frame 930 as shown in equation (4).

Figure 11:
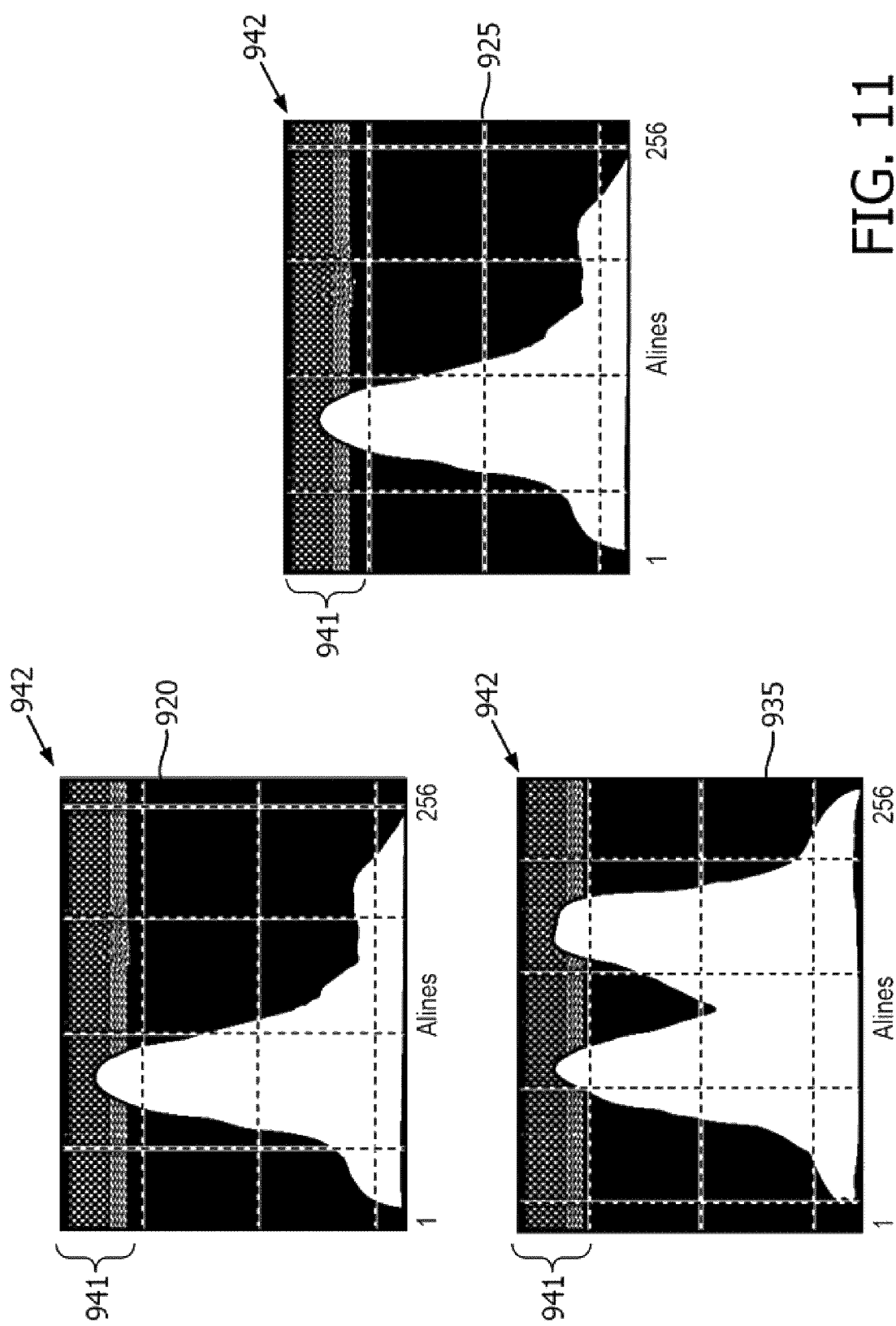
FIG. 11 illustrates a masked reference frame in a stage of ringdown reduction according to embodiments of the present disclosure.

FIG. 11 illustrates a masked reference frame 925 in a stage of ringdown reduction according to embodiments of the present disclosure. The masked reference frame 925 corresponds to a masked reference frame $R_0'$ at the output of the multiplication component 532. The masked reference frame 925 is generated by applying the threshold mask 935 to the reference frame 920.

Figure 12:
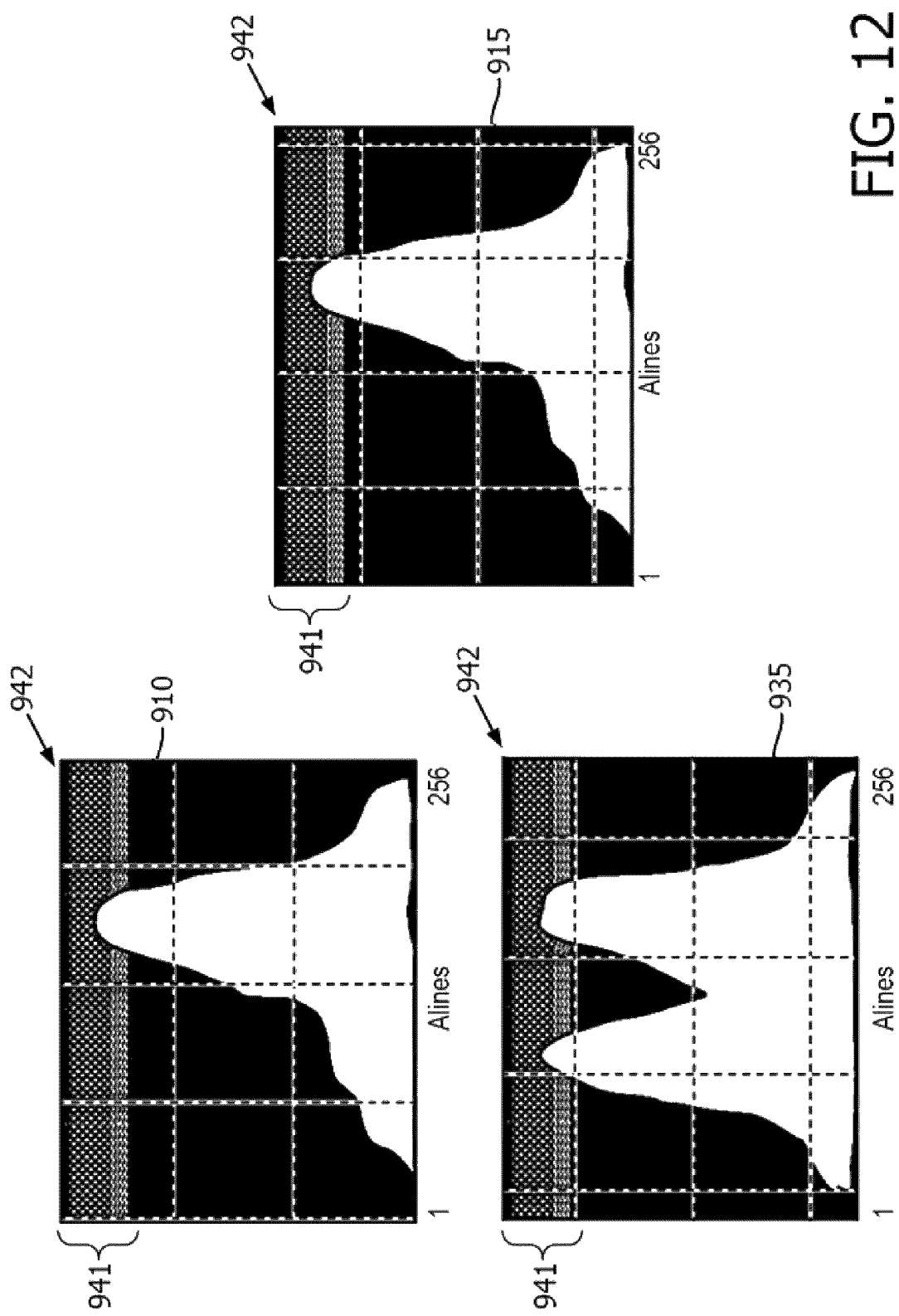
FIG. 12 illustrates a masked current frame in a stage of ringdown reduction according to embodiments of the present disclosure.

FIG. 12 illustrates a masked current frame 915 in a stage of ringdown reduction according to embodiments of the present disclosure. The masked current frame 915 corresponds to a masked current frame RF' at the output of the multiplication component 530. The masked current frame 915 is generated by applying the threshold mask 935 to the current frame 910.

Figure 13:
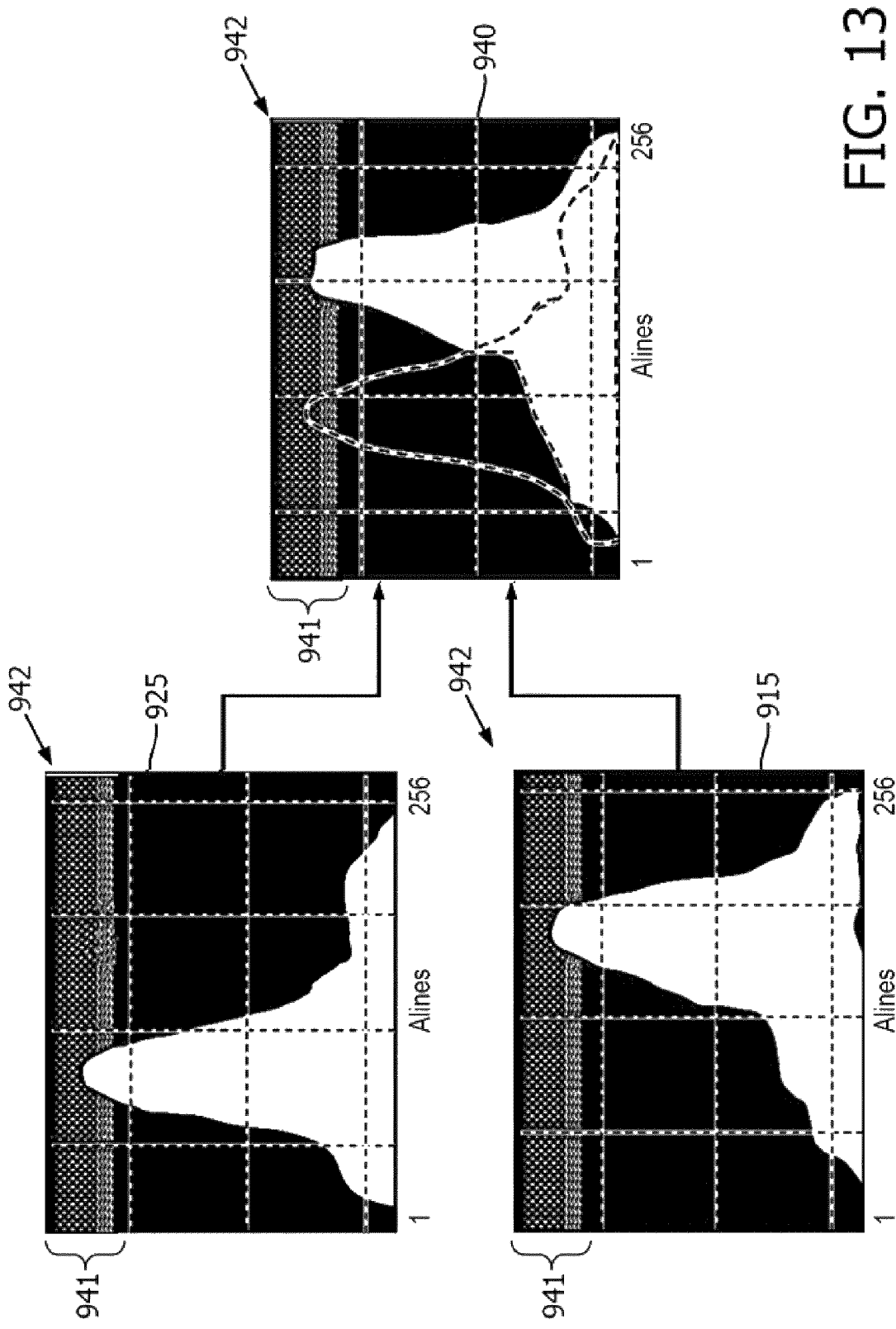
FIG. 13 illustrates a masked reference frame, a masked current frame, and a comparator mask in a stage of ringdown reduction according to embodiments of the present disclosure.

FIG. 13 illustrates the masked reference frame 925, the masked current frame 915, and a comparator mask 940 in a stage of ringdown reduction according to embodiments of the present disclosure. The comparator mask 940 corresponds to a comparator mask $M_C$ at the output of the comparator mask generator 534. The comparator mask 940 is generated from the masked current frame 915 and the masked reference frame 925 according to equation (5).

Figure 14:
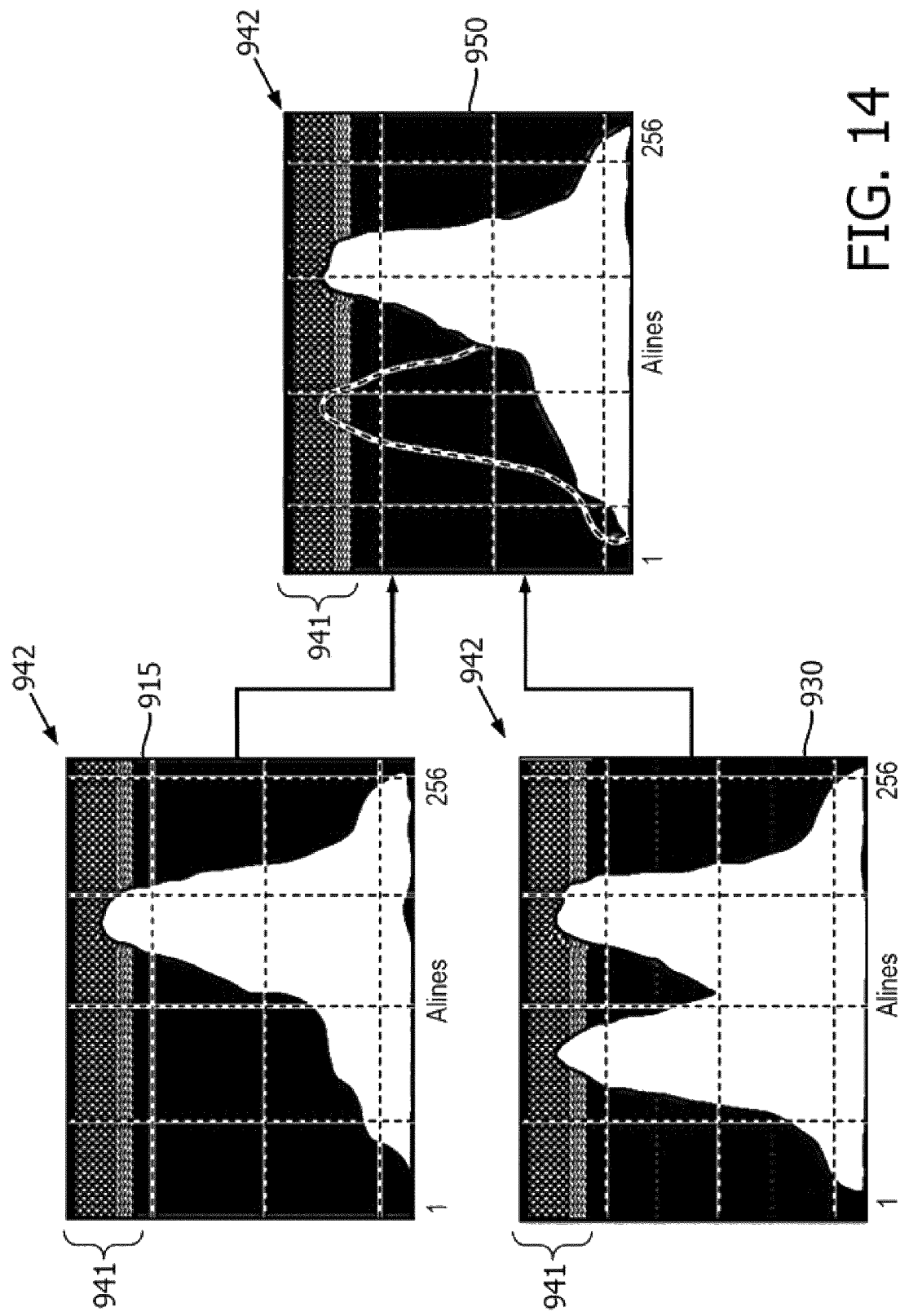
FIG. 14 illustrates a masked current frame, a difference frame, and a ringdown-reduced frame in a stage of ringdown reduction according to embodiments of the present disclosure.

FIG. 14 illustrates the masked current frame 915, the difference frame 930, and a ringdown-reduced frame 950 in a stage of ringdown reduction according to embodiments of the present disclosure. The ringdown-reduced frame 950 corresponds to a ringdown-reduced frame D at the output of the data selector 540. The ringdown-reduced frame 950 is generated from the masked current frame 915 and the difference frame 930 according to equation (7).

Figure 15:
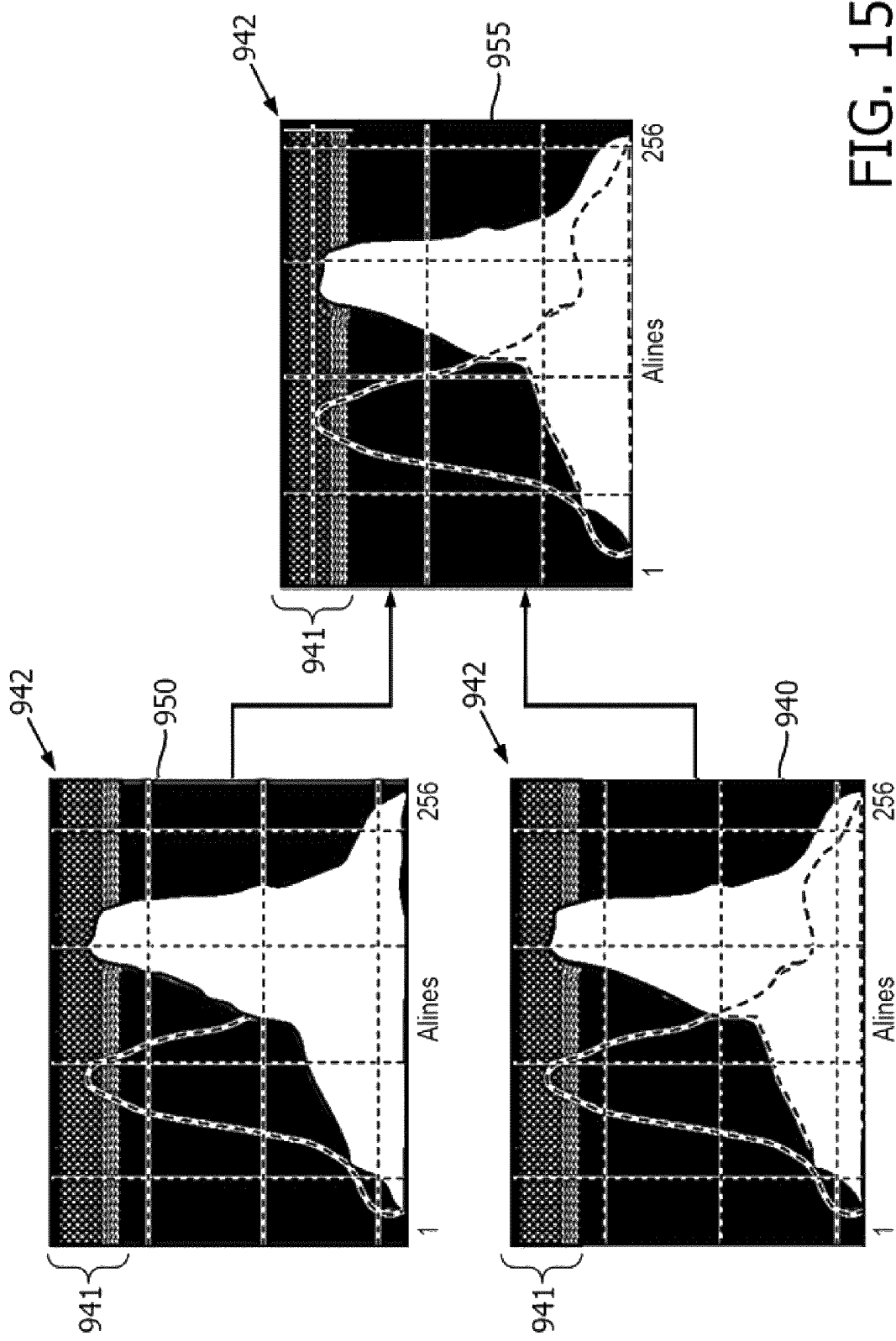
FIG. 15 illustrates a ringdown-reduced frame, a comparator mask, and a masked ringdown-reduced frame in a stage of ringdown reduction according to embodiments of the present disclosure.

FIG. 15 illustrates the ringdown-reduced frame 950, the comparator mask 940, and a masked ringdown-reduced frame 955 in a stage of ringdown reduction according to embodiments of the present disclosure. The masked ringdown-reduced frame 955 corresponds to a masked ringdown-reduced frame D' at the output of the data selector 540. The masked ringdown-reduced frame 955 is generated by applying the comparator mask 940 to the ringdown-reduced frame 950. As shown, the ringdown distortion has been removed from the ringdown region 941 of the masked ringdown-reduced frame 955 after the selection and the masking.

Figure 16:
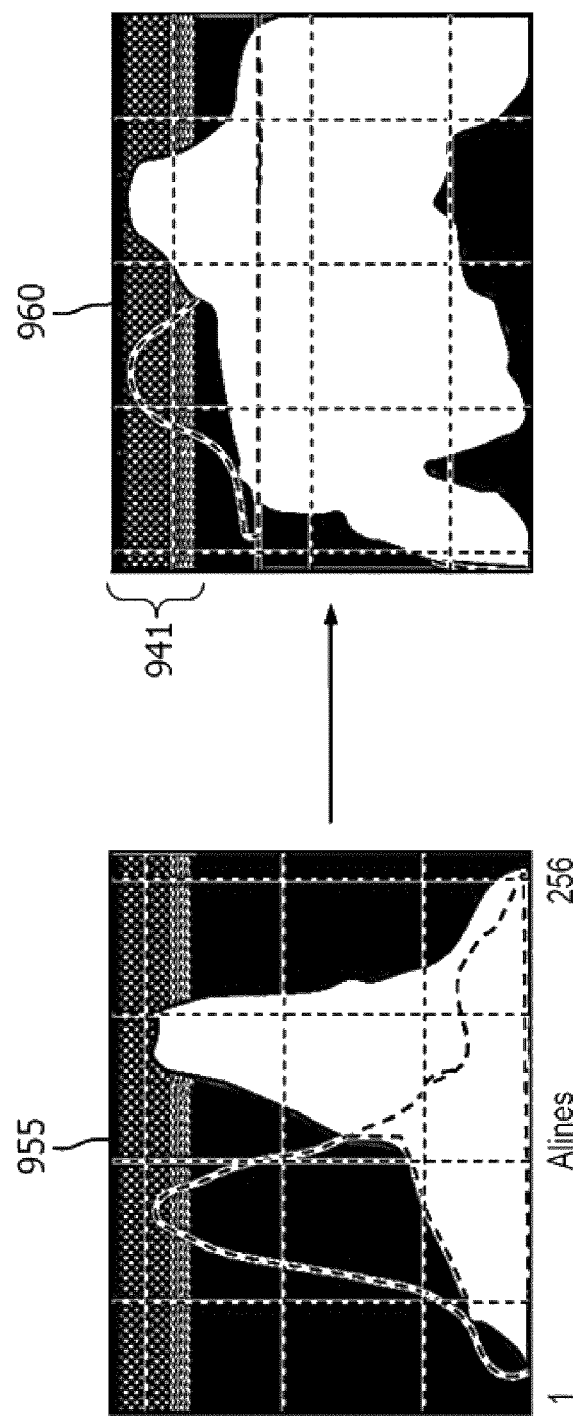
FIG. 16 illustrates a masked ringdown-reduced frame and a corrected complete frame in a stage of ringdown reduction according to embodiments of the present disclosure.

FIG. 16 illustrates a masked ringdown-reduced frame 955 and a corrected complete frame 960 in a stage of ringdown reduction according to embodiments of the present disclosure. The corrected complete frame 960 corresponds to an output frame O at the output of the tapering component 516. The corrected complete frame 960 is generated from the masked ringdown-reduced frame 955 and an original complete frame corresponding to the current frame 910 according to equations (13) and (14).

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of reducing ringdown artifacts in an ultrasound imaging system, comprising:
   obtaining a plurality of frames of samples including tissue information and a ringdown component;
   determining a reference frame based on the plurality of frames to approximate the ringdown component;
   subtracting the reference frame from a current frame of the plurality of frames to produce a difference frame;
   computing a threshold mask from the difference frame;
   applying the threshold mask to the current frame to produce a masked current frame;
   selecting between the masked current frame and the difference frame to obtain a ringdown-reduced frame to represent the tissue information; and
   forming an ultrasound image from the ringdown-reduced frame.

2. The method of claim 1, further comprising clipping magnitudes of the difference frame.

3. The method of claim 1, wherein the computing the threshold mask includes:
   determining whether a first absolute magnitude of the difference frame is less than a threshold;
   setting a mask value of the threshold mask to zero when the first absolute magnitude is less than the threshold; and
   setting the mask value to one when the first absolute magnitude is greater than or equal to the threshold.

4. The method of claim 1, wherein the performing the minimum selection includes:
   determining whether a second absolute magnitude of a first sample of the masked current frame is less than a third absolute magnitude of a second sample of the difference frame;
   selecting the first sample to produce a third sample in the ringdown-reduced frame when the second absolute magnitude is less than the third absolute magnitude; and
   selecting the second sample to produce the third sample in the ringdown-reduced frame when the third absolute magnitude is greater than or equal to the second absolute magnitude.

5. The method of claim 1, further comprising:
   applying the threshold mask to the reference frame to produce a masked reference frame;
   determining whether a second absolute magnitude of the masked current frame is greater than or equal to a third absolute magnitude of the masked reference frame; and
   setting a first sample of the ringdown-reduced frame to a value of zero when the second absolute magnitude is less than the third absolute magnitude.

6. The method of claim 5, further comprising reducing the third absolute magnitude by a third factor prior to determining whether the second absolute magnitude of the masked current frame is greater than or equal to the third absolute magnitude of the masked reference frame.

7. A method of reducing ringdown artifacts in an ultrasound imaging system, comprising:
   obtaining a plurality of frames of samples including tissue information and a ringdown component;
   determining a reference frame based on the plurality of frames to approximate the ringdown component;
   subtracting the reference frame from a current frame of the plurality of frames to produce a difference frame;
   selecting between the current frame and the difference frame to obtain a ringdown-reduced frame to represent the tissue information;
   forming an ultrasound image from the ringdown-reduced frame;
   further comprising applying an A-line filter to the ringdown-reduced frame prior to forming the ultrasound image.

8. A method of reducing ringdown artifacts in an ultrasound imaging system, comprising:
   obtaining a plurality of frames of samples including tissue information and a ringdown component;
   determining a reference frame based on the plurality of frames to approximate the ringdown component;
   subtracting the reference frame from a current frame of the plurality of frames to produce a difference frame;
   selecting between the current frame and the difference frame to obtain a ringdown-reduced frame to represent the tissue information;
forming an ultrasound image from the ringdown-reduced frame,
   wherein the obtaining the plurality of frames includes:
   receiving a complete frame of samples; and
   selecting a portion of the complete frame to obtain the current frame according to a ringdown depth;
   wherein the forming the ultrasound image includes:
   multiplying the ringdown-reduced frame by a first tapering factor to produce a tapered ringdown-reduced frame;
   multiplying the complete frame by a second tapering factor to produce a tapered complete frame;
   forming a first portion of the ultrasound image corresponding to the ringdown depth by summing the tapered ringdown-reduced frame and a second portion of the tapered complete frame corresponding to the ringdown depth; and
   forming a remaining portion of the ultrasound image from the tapered complete frame.

9. A method of reducing ringdown artifacts in an ultrasound imaging system, comprising:
   obtaining a plurality of frames of samples including tissue information and a ringdown component;
   determining a reference frame based on the plurality of frames to approximate the ringdown component;
   subtracting the reference frame from a current frame of the plurality of frames to produce a difference frame;

selecting between the current frame and the difference frame to obtain a ringdown-reduced frame to represent the tissue information;
forming an ultrasound image from the ringdown-reduced frame;
further comprising assigning a lower significant bit of a first sample of the reference frame to a bit value of zero prior to subtracting the reference frame from the current frame.

10. A method of reducing ringdown artifacts in an ultrasound imaging system, comprising:
obtaining a plurality of frames of samples including tissue information and a ringdown component;
determining a reference frame based on the plurality of frames to approximate the ringdown component;
subtracting the reference frame from a current frame of the plurality of frames to produce a difference frame;
selecting between the current frame and the difference frame to obtain a ringdown-reduced frame to represent the tissue information;
forming an ultrasound image from the ringdown-reduced frame
wherein the determining the reference frame includes:
multiplying the current frame by a first coefficient to produce a weighted current frame;
multiplying a previous averaged frame by a second coefficient to produce a weighted previous averaged frame;
updating the previous averaged frame to a current averaged frame by summing the weighted current frame and the weighted previous averaged frame;
assigning the current averaged frame to the reference frame;
wherein the summing the weighted current frame and the weighted previous averaged frame produces a first frame, and wherein the updating the previous averaged frame to the current averaged frame includes:
subtracting the previous averaged frame from the first frame to produce a second frame;
multiplying the second frame by a rate limit factor to produce a third frame;
summing the third frame and the previous averaged frame to produce a fourth frame;
determining whether a first sample in the second frame is greater than a snap threshold;
updating a second sample of the current averaged frame with a third sample of the fourth frame when the first sample is greater the snap threshold; and
updating the second sample with a fourth sample of the first frame when the first sample is less than or equal to the snap threshold.

11. The method of claim 10, wherein the updating the previous averaged frame to the current averaged frame further includes:
scaling the third sample with a range taper factor prior to updating second sample of the current averaged frame with the third frame when the first sample is greater than the snap threshold; and
scaling the fourth frame with the range taper factor prior to updating the current averaged frame with the fourth sample when the first sample is less than or equal to the snap threshold.

12. An ultrasound image processing system comprising:
an interface operable to receive a plurality of frames of samples including tissue information and a ringdown component; and
a processing unit coupled to the interface and configured to:
determine a reference frame based on the plurality of frames to approximate the ringdown component;
compute a difference frame based on a current frame of the plurality of frames and the reference frame;
compute a threshold mask from the difference frame according to a threshold;
apply the threshold mask to the current frame to produce a masked current frame;
select between the masked current frame and the difference frame to obtain a ringdown-reduced frame to represent the tissue information.

13. The ultrasound image processing system of claim 12, wherein the processing unit is further configured to clip magnitudes of the difference frame.

14. The ultrasound image processing system of claim 12, wherein the processing unit is further configured to:
determine whether a first absolute magnitude of the difference frame is less than the threshold;
set a mask value of the threshold mask to a first value when the first absolute magnitude is less than the threshold; and
set the mask value to a second value when the first absolute magnitude is greater than or equal to the threshold.

15. The ultrasound image processing system of claim 12, wherein the processing unit is further configured to:
determine whether a second absolute magnitude of a first sample of the masked current frame is less than a third absolute magnitude of a second sample of the difference frame;
select the first sample to produce a third sample in the ringdown-reduced frame when the second absolute magnitude is less than the third absolute magnitude; and
select the second sample to produce the third sample in the ringdown-reduced frame when the third absolute magnitude is greater than or equal to the second absolute magnitude.

16. The ultrasound image processing system of claim 15, wherein the processing unit is further configured to:
apply the threshold mask to the reference frame to produce a masked reference frame;
determine whether a second absolute magnitude of the masked current frame is greater than or equal to a third absolute magnitude of the masked reference frame; and
set a first sample of the ringdown-reduced frame to a value of zero when the second absolute magnitude is less than the third absolute magnitude.

17. The ultrasound image processing system of claim 16, wherein the interface is further configured receive a complete frame, wherein the current frame is a portion within a ringdown depth of the complete frame, and wherein the processing unit is further configured to:
multiply the ringdown-reduced frame by a first tapering factor to produce a tapered ringdown-reduced frame;
multiply the complete frame by a second tapering factor to produce a tapered complete frame;
forming a first portion of an image corresponding to the ringdown depth by summing the tapered ringdown-reduced frame and a second portion of the tapered complete frame corresponding to the ringdown depth; and
forming a remaining portion of an image from the tapered complete frame.

18. The ultrasound image processing system of claim 17, wherein the processing unit is further configured to apply an A-line filter to the ringdown-reduced frame prior to multiplying the ringdown-reduced frame with the first tapering factor.

\* \* \* \* \*